(12) United States Patent
Foschini et al.

(10) Patent No.: US 12,142,386 B2
(45) Date of Patent: Nov. 12, 2024

(54) SENSOR-BASED MACHINE LEARNING IN A HEALTH PREDICTION ENVIRONMENT

(71) Applicant: Evidation Health, Inc., San Mateo, CA (US)

(72) Inventors: Luca Foschini, Santa Barbara, CA (US); Eamon Caddigan, Philadelphia, PA (US); Raghunandan Melkote Kainkaryam, Cincinnati, OH (US)

(73) Assignee: EVIDATION HEALTH, INC., San Mateo, CA (US)

( * ) Notice: Subject to any disclaimer, the term of this patent is extended or adjusted under 35 U.S.C. 154(b) by 0 days.

(21) Appl. No.: 17/968,413

(22) Filed: Oct. 18, 2022

(65) Prior Publication Data

US 2023/0043921 A1 Feb. 9, 2023

Related U.S. Application Data

(63) Continuation-in-part of application No. 16/953,256, filed on Nov. 19, 2020, now abandoned, which is a
(Continued)

(51) Int. Cl.
  G16H 50/80 (2018.01)
  G06F 3/01 (2006.01)
  G06N 20/00 (2019.01)

(52) U.S. Cl.
  CPC ............ *G16H 50/80* (2018.01); *G06F 3/015* (2013.01); *G06N 20/00* (2019.01)

(58) Field of Classification Search
  CPC ........ G16H 50/80; G16H 40/67; G16H 50/20; G16H 50/30; G16H 50/70; G16H 15/00;
(Continued)

(56) References Cited

U.S. PATENT DOCUMENTS

| 6,947,953 B2 | 9/2005 | Herzenberg et al. |
| 7,937,461 B2 | 5/2011 | Kutzik et al. |

(Continued)

FOREIGN PATENT DOCUMENTS

| IN | 202041010784 | 11/2020 |
| WO | WO-2006031888 A2 | 3/2006 |

(Continued)

OTHER PUBLICATIONS

C. Jia, Q., Guo, Y., Wang, G., & Barnes, S. J. (2020). Big data analytics in the fight against major public health incidents (including COVID-19): A conceptual framework. International Journal of Environmental Research and Public Health, 17(17), 6161. (Year: 2020).*

(Continued)

*Primary Examiner* — Amber A Misiaszek
(74) *Attorney, Agent, or Firm* — WILSON SONSINI GOODRICH & ROSATI

(57) ABSTRACT

A machine learning prediction system can analyze a dataset of users with self-reported symptoms and associated data from a wearable device to impact measure the impact of an acute health condition (such as the flu) at the population level. The machine learning prediction system can train a machine learning model to recognize individual acute health condition patterns based on differences in user activity with respect to the characteristics of determined baseline periods. For example, per-individual normalized change with respect to baseline aggregated at the population level can be used to determine individual acute health condition patterns and predict the onset of certain acute health conditions using a trained machine learning model. In response to predictions, the machine learning prediction system can take interventions to manage the impact of a predicted acute health condition on an individual.

24 Claims, 19 Drawing Sheets

Related U.S. Application Data continuation of application No. 14/977,194, filed on Dec. 21, 2015, now abandoned.

(58) Field of Classification Search
CPC ........ G16H 40/20; G16H 40/63; G06N 20/00; G06N 3/0454; Y02A 90/10
See application file for complete search history.

(56) References Cited

U.S. PATENT DOCUMENTS

| | | |
|---|---|---|
| 8,392,215 B2 | 3/2013 | Tawil |
| 8,930,218 B1 | 1/2015 | Oakley et al. |
| 9,710,764 B1 | 7/2017 | Hodjat et al. |
| 9,760,422 B2 | 9/2017 | Chen et al. |
| 10,327,697 B1 | 6/2019 | Stein et al. |
| 10,524,697 B2 | 1/2020 | Gubbi Lakshminarasimha et al. |
| 11,056,242 B1* | 7/2021 | Jain .................. G16H 10/60 |
| 11,127,506 B1* | 9/2021 | Jain .................. H04W 4/021 |
| 11,387,000 B2 | 7/2022 | Saliman et al. |
| 11,468,992 B2 | 10/2022 | Pulicharam et al. |
| 11,471,115 B2 | 10/2022 | Rance et al. |
| 2001/0003099 A1 | 6/2001 | Von Kohorn |
| 2005/0228691 A1 | 10/2005 | Paparo |
| 2006/0084847 A1* | 4/2006 | Reed .................. G06F 15/173 600/595 |
| 2007/0288277 A1 | 12/2007 | Neuhauser et al. |
| 2008/0104167 A1 | 5/2008 | Cohen et al. |
| 2008/0146334 A1 | 6/2008 | Kil |
| 2008/0154707 A1 | 6/2008 | Mittal et al. |
| 2008/0214903 A1 | 9/2008 | Orbach |
| 2008/0319786 A1 | 12/2008 | Stivoric et al. |
| 2009/0006457 A1 | 1/2009 | Stivoric et al. |
| 2009/0055854 A1 | 2/2009 | Wright et al. |
| 2009/0070797 A1 | 3/2009 | Ramaswamy et al. |
| 2009/0138415 A1 | 5/2009 | Lancaster |
| 2009/0299767 A1 | 12/2009 | Michon et al. |
| 2011/0066464 A1 | 3/2011 | George |
| 2011/0184250 A1 | 7/2011 | Schmidt et al. |
| 2012/0046966 A1 | 2/2012 | Chang et al. |
| 2012/0124099 A1 | 5/2012 | Stewart |
| 2012/0246102 A1 | 9/2012 | Sudharsan |
| 2012/0278134 A1 | 11/2012 | Papay et al. |
| 2013/0004473 A1 | 1/2013 | Kochel et al. |
| 2013/0096943 A1 | 4/2013 | Carey et al. |
| 2013/0197894 A1 | 8/2013 | Sablinski |
| 2013/0216989 A1 | 8/2013 | Cuthbert |
| 2014/0005502 A1 | 1/2014 | Klap et al. |
| 2014/0095417 A1 | 4/2014 | Herz et al. |
| 2014/0129247 A1 | 5/2014 | Op Den Buijs et al. |
| 2014/0188512 A1 | 7/2014 | Parker et al. |
| 2014/0229418 A1 | 8/2014 | Graham, II et al. |
| 2014/0278449 A1 | 9/2014 | Kharraz Tavakol |
| 2014/0315168 A1 | 10/2014 | Movellan et al. |
| 2014/0344013 A1 | 11/2014 | Karty et al. |
| 2015/0006456 A1 | 1/2015 | Sudharsan |
| 2015/0163121 A1 | 6/2015 | Mahaffey et al. |
| 2015/0242518 A1 | 8/2015 | Rosenbaum et al. |
| 2015/0243180 A1 | 8/2015 | Kim et al. |
| 2016/0012194 A1* | 1/2016 | Prakash ............. G06Q 30/0601 705/2 |
| 2016/0089089 A1 | 3/2016 | Kakkar et al. |
| 2016/0142894 A1 | 5/2016 | Papakonstantinou et al. |
| 2016/0283686 A1 | 9/2016 | Hu et al. |
| 2016/0328991 A1 | 11/2016 | Simpson et al. |
| 2016/0357173 A1 | 12/2016 | Foschini et al. |
| 2016/0361020 A1 | 12/2016 | LeBoeuf et al. |
| 2017/0053091 A1 | 2/2017 | Holmes et al. |
| 2017/0140109 A1 | 5/2017 | Kheifetz et al. |
| 2017/0188841 A1 | 7/2017 | Ma et al. |
| 2017/0206795 A1* | 7/2017 | Kaleal, III .............. G06T 19/00 |
| 2017/0245808 A1 | 8/2017 | Jain et al. |
| 2017/0249434 A1 | 8/2017 | Brunner |
| 2017/0293846 A1 | 10/2017 | Zyglowicz et al. |
| 2018/0330824 A1 | 11/2018 | Athey et al. |
| 2018/0338733 A1 | 11/2018 | Jain et al. |
| 2018/0344215 A1 | 12/2018 | Ohnemus et al. |
| 2018/0350451 A1 | 12/2018 | Ohnemus et al. |
| 2019/0019581 A1 | 1/2019 | Vaughan et al. |
| 2019/0043337 A1 | 2/2019 | Liu et al. |
| 2019/0066845 A1 | 2/2019 | Roy et al. |
| 2019/0076031 A1* | 3/2019 | Valys .................. A61B 5/02405 |
| 2019/0209022 A1* | 7/2019 | Sobol .................. A61B 5/02055 |
| 2019/0245824 A1 | 8/2019 | Hiir et al. |
| 2019/0287660 A1 | 9/2019 | Oliveira et al. |
| 2019/0287669 A1 | 9/2019 | Sun et al. |
| 2019/0339291 A1 | 11/2019 | Edmonds et al. |
| 2019/0355472 A1 | 11/2019 | Kutzko |
| 2019/0385711 A1 | 12/2019 | Shriberg et al. |
| 2020/0034585 A1 | 1/2020 | Lu et al. |
| 2020/0135334 A1 | 4/2020 | Rajasekhar et al. |
| 2020/0161005 A1 | 5/2020 | Lyman et al. |
| 2020/0273578 A1* | 8/2020 | Kutzko .................. H04L 9/0637 |
| 2020/0302775 A1 | 9/2020 | Liu et al. |
| 2020/0372369 A1 | 11/2020 | Gong et al. |
| 2021/0011443 A1 | 1/2021 | McNamara et al. |
| 2021/0012902 A1 | 1/2021 | Chawla et al. |
| 2021/0038163 A1 | 2/2021 | Agrawal et al. |
| 2021/0042667 A1 | 2/2021 | Ghosh et al. |
| 2021/0113099 A1 | 4/2021 | Rogers et al. |
| 2021/0117417 A1 | 4/2021 | Hendrickson et al. |
| 2021/0118136 A1 | 4/2021 | Hassan-Shafique et al. |
| 2021/0151194 A1 | 5/2021 | Foschini et al. |
| 2021/0151198 A1 | 5/2021 | Sabeti et al. |
| 2021/0158214 A1 | 5/2021 | Witt et al. |
| 2021/0166803 A1 | 6/2021 | Ellis et al. |
| 2021/0174919 A1 | 6/2021 | Vaughan |
| 2021/0182708 A1 | 6/2021 | Park et al. |
| 2021/0201129 A1 | 7/2021 | Schmude et al. |
| 2021/0204914 A1 | 7/2021 | Meral et al. |
| 2021/0241923 A1 | 8/2021 | Foschini et al. |
| 2021/0319887 A1 | 10/2021 | Derrick, Jr. et al. |
| 2022/0068494 A1 | 3/2022 | Op Den Buijs et al. |
| 2022/0343160 A1 | 10/2022 | Park et al. |
| 2023/0033835 A1 | 2/2023 | Rathore et al. |
| 2023/0090138 A1 | 3/2023 | Clay et al. |
| 2023/0187073 A1 | 6/2023 | Foschini et al. |
| 2023/0245777 A1 | 8/2023 | Foschini et al. |
| 2024/0047042 A1 | 2/2024 | Daza |

FOREIGN PATENT DOCUMENTS

| | | |
|---|---|---|
| WO | WO-2014039881 A1 | 3/2014 |
| WO | WO-2019165004 A1 | 8/2019 |
| WO | WO-2021127566 A1 | 6/2021 |
| WO | WO-2021154401 A1 | 8/2021 |
| WO | WO-2021222601 A1 | 11/2021 |
| WO | WO-2022200985 A1 | 9/2022 |
| WO | WO-2023044052 A1 | 3/2023 |
| WO | WO-2023114779 A1 | 6/2023 |
| WO | WO-2023150428 A1 | 8/2023 |

OTHER PUBLICATIONS

Althouse et al.: Enhancing disease surveillance with novel data streams: challenges and opportunities. EPJ Data Sci. 4(1):17, pp. 1-8 doi:10.1140/epjds/s13688-015-0054-0 (2015).

Cao et al.: DeepMood: Modeling Mobile Phone Typing Dynamics for Mood Detection. arXiv:1803.08986, pp. 1-9 doi:10.1145/3097983. 3098086 (2018).

Co-pending U.S. Appl. No. 17/111,765, inventors Foschini; Luca et al., filed Dec. 4, 2020.

Daly et al.: Risk stratification and daily symptom monitoring for oncology patients. Journal of Clinical Oncology 37(15)Suppl., p. 6535 DOI:10.1200/JCO.2019.37.15_suppl.6535 (2019).

Element AI: Element AI makes its BAyesian Active Learning library open source. (Retrieved online on Jan. 21, 2021), pp. 1-6 URL: https://www.elementai.com/news/2019/element-ai-makes-its-bayesian-active-learning-library-open-source (2019).

Evidation Health: Achievement. Publication Date Unknown, six pages, [Retrieved online Nov. 4, 2020] URL: https://www.myachievement.com/.

(56) References Cited

OTHER PUBLICATIONS

Gal et al.: Bayesian convolutional neural networks with Bernoulli approximate variational inference. ICLR workshop track arXiv:1506.02158, pp. 1-12 doi:10.48550/ARXIV.1506.02158 (2016).
Gal et al.: Deep Bayesian Active Learning with Image Data. arXiv:1703.02910, pp. 1-10 doi:10.48550/ARXIV.1703.02910 (2017).
Gal et al.: Dropout as a Bayesian approximation: Representing model uncertainty in deep learning. International Conference on Machine Learning, pp. 1-10 URL: http://proceedings.mlr.press/v48/gal16.pdf (2016).
Henning: What is Syndromic Surveillance?. MMWR Suppl. 53:5-11 (2004).
Hochreiter et al. Long Short-Term Memory. Neural Computation 9(8):1735-1780 (1997).
Houlsby et al.: Bayesian Active Learning for Classification and Preference Learning. arXiv:1112.5745, pp. 1-17 doi:10.48550/ARXIV.1112.5745 (2011).
Li et al.: Digital Health: Tracking Physiomes and Activity Using Wearable Biosensors Reveals Useful Health-Related Information. PLoS Biology, pp. 1-30 DOI:10.1371/journal.pbio.2001402(2017).
Nelson et al.: Continuous, objective measurement of physical activity during chemotherapy for breast cancer: the Activity in Treatment pilot study. Transl Behav Med. 10(4):1031-1038 doi:10.1093/tbm/ibz079 (2020).
PCT/US2020/064369 International Search Report and Written Opinion dated Mar. 2, 2021.
Radin et al: Harnessing wearable device data to improve state-level real-time surveillance of influenza-like illness in the USA: a population-based study. Lancet Digit Health 2(2):e85-e93 doi:10.1016/S2589-7500(19)30222-5 (2020).
Schroeder et al.: Examining Self-Tracking by People with Migraine: Goals, Needs, and Opportunities in a Chronic Health Condition. DIS 2018, pp. 135-148 DOI:10.1145/3196709.3196738 (2018).
Simonsen et al.: Infectious Disease Surveillance in the Big Data Era: Towards Faster and Locally Relevant Systems. J Infect Dis. 214(suppl_4):S380-S385 doi:10.1093/infdis/jiw376 (2016).
Turner: New directions in communications (or Which way to the Information Age?). IEEE Communications Magazine 24(10):8-15 doi:10.1109/MCOM.1986.1092946 (1986).
U.S. Appl. No. 14/977,194 Final Office Action dated Dec. 16, 2016.
U.S. Appl. No. 14/977,194 Final Office Action dated Jul. 12, 2018.
U.S. Appl. No. 14/977,194 Final Office Action dated May 21, 2020.
U.S. Appl. No. 14/977,194 Non-Final Office Action dated Aug. 30, 2017.
U.S. Appl. No. 14/977,194 Non-Final Office Action dated Feb. 25, 2016.
U.S. Appl. No. 14/977,194 Non-Final Office Action dated Sep. 26, 2019.
U.S. Appl. No. 16/926,510 Non-Final Office Action dated Jul. 8, 2022.
U.S. Food & Drug Administration: Real-World Evidence, pp. 1-3 [Retrieved online Nov. 4, 2020] URL: https://www.fda.gov/science-research/science-and-research-special-topics/real-world-evidence (published Mar. 23, 2020).
Wang et al.: Unsupervised learning of disease progression models. KDD '14: Proceedings of the 20th ACM SIGKDD international conference on Knowledge discovery and data mining, pp. 85-94 URL:https://doi.org/10.1145/2623330.2623754 (Aug. 2014).
U.S. Appl. No. 17/946,975 Non-Final Office Acton dated Nov. 17, 2022.
PCT/US2022/043874 International Search Report and Written Opinion dated Nov. 17, 2022.
U.S. Appl. No. 17/946,975 Final Office Action dated May 5, 2023.
Co-pending U.S. Appl. No. 18/148,991, inventors Foschini; Luca et al., filed Dec. 30, 2022.
Co-pending U.S. Appl. No. 18/156,010, inventors Foschini; Luca et al., filed Jan. 18, 2023.
Homayounfar et al.: Data mining research trends in computerized patient records. 2011 Federated Conference on Computer Science and Information Systems (FedCSIS), pp. 133-139 (2011).

Mezlini et al.: Estimating the Burden of Influenza-like Illness on Daily Activity at the Population Scale Using Commercial Wearable Sensors. JAMA Netw Open. 5(5):e2211958:1-12 doi:10.1001/jamanetworkopen.2022.11958 (2022).
Pavel et al.: Behavioral Informatics and Computational Modeling in Support of Proactive Health Management and Care. IEEE Transactions on Biomedical Engineering. 62(12):2763-2775 doi:10.1109/TBME.2015.2484286 (2015).
PCT/US2022/081465 Invitation to Pay Additional Fees dated Mar. 2, 2023.
Pentland: Healthwear: medical technology becomes wearable. Computer 37(5), pp. 42-49 doi:10.1109/MC.2004.1297238 (2004).
Qayyum et al.: Secure and Robust Machine Learning for Healthcare: A Survey. IEEE Reviews in Biomedical Engineering, vol. 14, pp. 156-188 doi:10.1109/RBME.2020.3013489 (2020).
U.S. Appl. No. 16/953,256 Non-Final Office Action dated Jan. 5, 2023.
U.S. Appl. No. 17/111,765 Non-Final Office Action dated Feb. 17, 2023.
U.S. Appl. No. 17/946,975 Non-Final Office Action restarting Office Action dated Nov. 17, 2022, mailed on Jan. 11, 2023.
U.S. Appl. No. 18/156,010 Non-Final Office Action dated Mar. 22, 2023.
Abeler et al., Sleep characteristics in adults with and without chronic musculoskeletal pain: The role of mental distress and pain catastrophizing. Clin J Pain. 2020; 36(9):707-715.
Altman et al., Sleep Disturbance after Hospitalization and Critical Illness: A Systematic Review. Ann Am Thorac Soc. 2017; pp. 1457-1468.
Amin et al., Personalized health monitoring using predictive analytics. 2019 IEEE Fifth International Conference on Big Data Computing Service and Applications (BigDataService), 8 pages (2019).
Appelboom et al., Mobile Phone-Connected Wearable Motion Sensors to Assess Postoperative Mobilization. JMIR mHealth and uHealth. 2015; 3(3):e78, pp. 1-12.
Araujo et al., Understanding variation in sets of N-of-1 trials. PloS one. 2016; 11(12):e0167167, pp. 1-24.
Arlot et al., A survey of cross-validation procedures for model selection. Statistics surveys. 2010; 4:40-79.
Arnold et al., Does physical activity increase after total hip or knee arthroplasty for osteoarthritis? a systematic review. J Orthop Sports Phys Ther. Jun. 2016;46(6):431-442.
Aronow et al., Estimating average causal effects under interference between units. arXiv preprint arXiv:13056156. 2013; 3(4):16, pp. 1-40.
Athey et al., Machine learning methods for estimating heterogeneous causal effects.arXiv:150401132v1 [statML] Apr. 5, 2015. 2015:1-24.
Atito et al.: MC-SSL0.0: Towards Multi-Concept Self-Supervised Learning. arXiv:2111.15340, 2021; pp. 1-17.
Avati et al., Improving palliative care with deep learning. BMC Med Inform Decis Mak. 18(Suppl 4):122, pp. 1-10 (2018).
Backman et al., Case studies, single-subject research, and N of 1 randomized trials: comparisons and contrasts. Am J Phys Med Rehabil. 1999;78(2):170-176.
Balandat et al., New tools for econometric analysis of high-frequency time series data-application to demand-side management in electricity markets. University of California, Berkeley. 2016; 221 pages.
Bang et al., Doubly robust estimation in missing data and causal inference models. Biometrics. 2005; 61(4):962-973.
Bang et al., Total hip and total knee arthroplasties: trends and disparities revisited. Am J Orthop . Sep. 2010;39(9):E95-102.
Bartlett et al., Organizational research: determining appropriate sample size in survey research. Inf Tech Learn and Perf J. 2001; 19(1):43-50.
Bender et al., On the dangers of stochasticparrots: Can language models be too big? Proceedings of the 2021 ACM Conference onFairness, Accountability, and Transparency. 2021; 610-623.
Bühlmann, Invariance, causality and robustness. Statistical Science. 2020;35(3):404-426.

(56) References Cited

OTHER PUBLICATIONS

Bindawas et al., Trajectories in functional recovery for patients receiving inpatient rehabilitation for unilateral hip or knee replacement. Arch Gerontol Geriatr. 2014;58(3):344-349.
Borbély, A two process model of sleep regulation. Hum neurobiol. 1982;1(3):195-204.
Bradshaw et al., Influenza Surveillance Using Wearable Mobile Health Devices. Online Journal of Public Health Informatics. 2019; 11(1):e249, pp. 1-4.
Brown et al., Language models are few-shot learners. Advances inneural information processing systems. 2020; 33:1877-1901.
Burg et al., Does Stress Result in You Exercising Less? Or Does Exercising Result in You Being Less Stressed? Or Is It Both? Testing the Bi-directional Stress-Exercise Association at the Group and Person (N of 1) Level. Ann Behav Med. 2017; 51(6): 799-809.
Carney et al., The consensus sleep diary: standardizing prospective sleep self-monitoring. Sleep. 2012;35(2):287-302.
Chen et al., A Scalable Tree Boosting System. Proceedings of the 22nd ACM SIGKDD International Conference on Knowledge Discovery and Data Mining. New York, NY, USA: ACM; 2016; pp. 785-794.
Chen et al., Making sense of mobile health data: an open architecture to improve individual- and population-level health. Journal of Medical Internet Research. 2012;14(4):e112, pp. 1-10.
Cheung et al., Are Nomothetic or Ideographic Approaches Superior in Predicting Daily Exercise Behaviors? Methods of Information in Medicine. 2017; 56(6):452-460.
Chevance, Day-to-day associations between sleep and physical activity: a set of person-specific analyses in adults with overweight and obesity. Journal of Behavioral Medicine. 2022;45(1):14-27.
Chinoy et al., Performance of seven consumer sleep-tracking devices compared with polysomnography. Sleep. 2021; 44(5):zsaa291, pp. 1-16.
Cohen et al., A digital health industry cohort across the health continuum. NPJ Digit Med. 2020; 3:68, pp. 1-10.
Coravos et al., Digital Medicine: A primer on measurement. Digit Biomark. 2019; 3(2):31-71.
Dawid et al., Identifying the consequences of dynamic treatment strategies: A decision—theoretic overview. Statistics Surveys. 2010; 4:184-231.
Dawid et al., Identifying the consequences of dynamic treatment strategies. Research Report, University College London. 2005; 38 pages.
Dawid, Influence diagrams for causal modelling and inference. International Statistical Review. 2002;70(2):161-189.
Daza, Causal analysis of self-tracked time series data using a counterfactual framework for N- of-1 trials. Methods Inf Med. 2018; (1):e10-e21.
Daza et al., Effects of sleep deprivation on blood glucose, food cravings, and affect in a non-diabetic: An N-of-1 randomized pilot study. Healthcare (Basel). 2019; 8(1):6, pp. 1-17.
Daza, Person as Population: A Longitudinal View of Single-Subject Causal Inference for Analyzing Self-Tracked Health Data. arXiv preprint arXiv:190103423. 2019, 18 pages.
Deering et al., Accelerating Research With Technology: Rapid Recruitment for a Large-Scale Web-Based Sleep Study. JMIR Res Protoc. 2019; 8(1):e10974, pp. 1-11.
Dolata et al., Influence of age on the outcome of rehabilitation after total hip replacement. Pol Orthop Traumatol. 2013; 78:109-113.
Dong et al., Familial natural short sleep mutations reduce Alzheimer pathology in mice. Iscience. 2022;25(4):103964, pp. 1-15.
Duan et al., Single-patient (n-of-1) trials: a pragmatic clinical decision methodology for patient-centered comparative effectiveness research. J Clin Epidemiol. 2013; 66(8):S21-S28.
Dyer et al., A critical review of the long-term disability outcomes following hip fracture. BMC Geriatr. 2016; 16:158, pp. 1-18.
Eichler, Causal inference in time series analysis. Causality: Statistical Perspectives and Applications. 2012:327-354.

Ei-Galaly et al., Can Machine-learning Algorithms Predict Early Revision TKA in the Danish Knee Arthroplasty Registry? Clin Orthop Relat Res. 2020; 478:2088-2101.
Enshaeifar et al., Machine learning methods for detecting urinary tract infection and analysing daily living activities in people with dementia. PLoS One. 2019; 14(1):e0209909, pp. 1-22.
Estrin, Small data, where n= me. Communications of the ACM. 2014;57(4):32-34.
Gabler et al., N-of-1 trials in the medical literature: a systematic review. Med Care. 2011;49(8):761-768.
Garfield, Sleep duration: A review of genome-wide association studies (GWAS) in adults from 2007 to 2020. Sleep Medicine Reviews. 2021; 56:101413, pp. 1-9.
Gastaldi, Shake-shake regularization. arXiv preprint arXiv: 1705. 07485. 2017; pp. 1-10.
Goldsack et al., Verification, analytical validation, and clinical validation (V3): the foundation of determining fit-for-purpose for Biometric Monitoring Technologies (BioMeTs). NPJ Digit Med. 2020; 3:55, pp. 1-10.
Goldsmith et al., Generalized multilevel function-on-scalar regression and principal component analysis. Biometrics. 2015;71(2):344-353.
Greenland et al., Confounding and collapsibility in causal inference. Statistical science. 1999:29-46.
Greenland et al., Identifiability, exchangeability and confounding revisited. Epidemiologic Perspectives & Innovations. 2009;6(1):4; pp. 1-9.
Guyatt et al., Determining optimal therapy—randomized trials in individual patients. N Engl J Med. 1986;314(14):889-892.
Guyatt et al., The n-of-1 Randomized Controlled Trial: Clinical Usefulness: Our Three-Year Experience. Annals of Internal Medicine. 1990;112(4):293-299.
Haberkamp et al., European regulators' views on a wearable-derived performance measurement of ambulation for Duchenne muscular dystrophy regulatory trials. Neuromuscul Disord. 2019; 29(7):514-516.
Haghayegh et al., Accuracy of wristband Fitbit models in assessing sleep: systematic review and meta-analysis. Journal of medical Internet research. 2019; 21(11):e16273, pp. 1-7.
Hallgrimsson et al., Learning Individualized Cardiovascular Responses from Large-scale Wearable Sensors Data. arXiv preprint arXiv:1812. 01696. 2018; pp. 1-5.
Hansen, The prognostic analogue of the propensity score. Biometrika. 2008;95(2):481-488.
He et al., The transcriptional repressor DEC2 regulates sleep length in mammals. Science. 2009;325(5942):866-870.
Hekler et al., Why we need a small data paradigm. BMC medicine. 2019;17(1):1-9.
Hernan et al., Estimating causal effects from epidemiological data. Journal of Epidemiology and Community Health. 2006;60(7):578-586.
Hirano et al., Estimation of causal effects using propensity score weighting: An application to data on right heart catheterization. Health Services and Outcomes research methodology. 2001;2(3):259-278.
Holland et al., Statistics and causal inference. Journal of the American Statistical Association. 1986;81 (396) :945-960.
Horne et al., A self-assessment questionnaire to determine morningness-eveningness in human circadian rhythms. International journal of chronobiology. 1976; author manuscript, 13pages.
Horvitz et al., A generalization of sampling without replacement from a finite universe. Journal of the American Statistical Association. 1952;47(260):663-685.
Hudgens et al., Toward causal inference with interference. J Am Stat Assoc. 2008; 103(482):832-842.
Jonker et al., Postoperative recovery of accelerometer-based physical activity in older cancer patients. Eur J Surg Oncol. 2020; 46(11):2083-2090.
Kalmbach et al., Genetic basis of chronotype in humans: insights from three landmark GWAS. Sleep. 2017;40(2) pp. 1-10.
Khosla et al., Consumer sleep technol-ogy: an American Academy of Sleep Medicine position statement. Journal of clinical sleep medicine. 2018; 14(5):877-880.

(56) References Cited

OTHER PUBLICATIONS

Kingma et al., Adam: A method for stochastic optimization. arXiv preprintarXiv: 1412.6980. 2014; pp. 1-15.
Kolbeinsson et al.: Self-supervision of wearable sensors time-series data for influenza detection. arXiv:2112.13755[cs.LG]. 2021; pp. 1-5.
Kravitz et al., Design and Implementation of N-of-1 Trials: A User's Guide. AHRQ Publication No. 13(14)-EHC122-EF. Rockville, MD: Agency for Healthcare Research and Quality; Feb. 2014. 94pages.
Kumar et al., Design, Recruitment, and Baseline Characteristics of a Virtual 1-Year Mental Health Study on Behavioral Data and Health Outcomes: Observational Study. JMIR Mental Health. 2020; 7(7):e17075, pp. 1-12.
Kuroda et al., Patient-related risk factors associated with less favourable outcomes following hip arthroscopy. Bone Joint J. 2020; 102-B(7):822-831.
Labrique et al., Best practices in scaling digital health in low and middle income countries. Global Health. 2018;14(1):103, pp. 1-8.
Li et al., Digital health: Tracking physiomes and activity using wearable biosensors reveals useful health-related information. PLOS Biology. 2017; 15(1): e2001402, pp. 1-30.
Liang et al., Accuracy of Fitbit Wristbands in Measuring Sleep Stage Transitions and the Effect of User-Specific Factors. JMIR Mhealth Uhealth. 2019; 7(6):e13384, pp. 1-13.
Lillie et al., The n-of-1 clinical trial: the ultimate strategy for individualizing medicine? Per Med. 2011;8(2):161-173.
Lin et al., Surgical Strategy for the Chronic Achilles Tendon Rupture. Biomed Res Int. 2016; 2016:1416971, pp. 1-8.
Lunceford et al., Stratification and weighting via the propensity score in estimation of causal treatment effects: A comparative study. Statistics in Medicine. 2004;23(19):2937-2960.
Lzmailova et al., Remote digital monitoring for medical product development. Clin Transl Sci. 2020; 14(1): 94-101.
Magaziner et al., Recovery after hip fracture: interventions and their timing to address deficits and desired outcomes—evidence from The Baltimore Hip Studies. Nestle Nutr Inst Workshop Ser. 2015;83:71-81.
Mahendraratnam et al., Determining Real-World Data's Fitness for Use and the Role of Reliability. Duke Margolis center for health policy, 54 pages (2019) Available at: https://healthpolicy.duke.edu/sites/default/files/2019-11/rwd_reliability.pdf.
Malenica et al., Adaptive Sequential Design for a Single Time-Series. arXiv:2102.00102 [math.ST]. 2021; pp. 1-64.
Mallinson et al., Subjective sleep measurement: comparing sleep diary to questionnaire. Nature and Science of Sleep. 2019; 11:197-206.
Marinsek et al., Measuring COVID-19 and influenza in the real world via person-generated health data. bioRχiv medRxiv preprint. 23pages (2020).
Matthews, Multi-period crossover trials. Stat Methods Med Res. 1994; 3(4):383-405.
Merrill et al., Self-supervised pretraining and transfer learning enable flu andcovid-19 predictions in small mobile sensing datasets. arXiv preprint arXiv:2205.13607. 2022; 11 pages.
Mezlini et al., Precision recruitment for high-risk participants in a COVID-19 cohort study Contemp Clin Trials Commun. 2023; 33:101113, pp. 1-4.
Mitchell et al., Model cards for model reporting. arXiv:1810.03993. 2019; pp. 1-10.
Montes et al., Step count reliability and validity of five wear-able technology devices while walking and jogging in both a free motion setting and on a treadmill. International Journal of Exercise Science. 2020;13(7):410-426.
Moraffah et al., Causal inference for time series analysis: Problems, methods and evaluation. Knowledge and Information Systems. 2021:1-45.
Mueller et al., Continuous monitoring of patient mobility for 18 months using inertial sensors following traumatic knee injury: A Case Study. Digit Biomark. 2018; 2(2):79-89.
Naughton, A starter kit for undertaking n-of-1 trials. European Health Psychologist. 2014;16(5):196-205.
Neto et al., On the analysis of personalized medication response and classification of case vs control patients in mobile health studies: the mPower case study. arXiv:1706.09574 [stat.AP]. 2017; pp. 1-27.
Neto et al., Towards personalized causal inference of medication response in mobile health: an instrumental variable approach for randomized trials with imperfect compliance. arXiv:1604.01055 [stat.AP]. 2016; pp. 1-38.
Neyman, On the application of probability theory to agricultural experiments. Essay on principles. Section 9. Statistical Science. 1923, tr 1990;5(4):465-480. Translated and edited by D.M. Dabrowska and T.P. Speed from the Polish original, which appeared in Roczniki Nauk Rolniczych Tom X (1923) 1-51 (Annals of Agricultural Sciences).
O'Driscoll et al., How well do activity monitors estimate energy expenditure? A systematic review and meta-analysis of the validity of current technologies. Br J Sports Med. Mar. 2020;54(6):332-340.
OECD. Health at a Glance 2019: OECD Indicators. Health at a Glance 2019. 2019; 243 pages DOI: 10.1787/19991312.
Orloff et al. The future of drug development: Advancing clinicaltrial design. Nature reviews Drug discovery, 2009; 8(12):949-957.
Passias et al., Total Knee Arthroplasty in Patients of Advanced Age: A Look at Outcomes and Complications. J Knee Surg. Jan. 2020;33(1):1-7.
Pearl, Causal diagrams for empirical research. Biometrika. 1995;82(4):669-688.
Pearl et al., Probabilistic evaluation of sequential plans from causal models with hidden variables. Appears in Proceedings of the Eleventh Conference on Uncertainty in Artificial Intelligence (UAI1995). 1995; pp. 444-453.
Piau et al., Current state of digital biomarker technologies for real-life, home-based monitoring of cognitive function for mild cognitive impairment to mild alzheimer disease and implications for clinical care: systematic review. J Med Internet Res. 2019;21(8):e12785, pp. 1-13.
Ponterotto, Qualitative research in counseling psychology: A primer on research paradigms and philosophy of science. Journal of Counseling Psychology. 2005;52(2):126-136.
Radin et al., Harnessing wearable device data to improve state-level real-time surveillance of influenza-like illness in the USA: a population-based study. The Lancet Digital Health. 2020; 2(2):E85-E93.
Rae et al. Scaling language models: Methods, analysis & insightsfrom training gopher. arXiv preprint arXiv:2112.11446. 2021; pp. 1-120.
Ramesh et al., Hierarchical text-conditionalimage generation with clip latents. arXiv:2204.06125 [cs.CV]. 2022; 27 pages.
Ramirez et al., Continuous Digital Assessment for Weight Loss Surgery Patients. Digit Biomark. 2020;4(1):13-20.
Reed et al., A generalist agent. arXiv preprintarXiv:2205.06175. 2022; pp. 1-42.
Robins, A new approach to causal inference in mortality studies with a sustained exposure period application to control of the healthy worker survivor effect. Mathematical Modelling. 1986;7(9-12):1393-1512.
Robins et al., Marginal structural models and causal inference in epidemiology. Epidemiology. 2000; 11:550-560.
Robins et al., Estimation of the causal effects of time-varying exposures. Longitudinal Data Analysis. 2009; Ch. 23, 553-599.
Robins, Marginal structural models. 1997 Proceedings of the section on Bayesian statistical science. 1997:1-10.
Roenneberg et al., Life between clocks: daily temporal patterns of human chronotypes. Journal of biological rhythms. 2003;18(1):80-90.
Rombach, High-resolution image syn-thesis with latent diffusion models. Proceedings of the IEEE/CVF Conference on ComputerVision and Pattern Recognition. 2022; 10684-10695.
Rosenbaum et al., The central role of the propensity score in observational studies for causal effects. Biometrika. 1983;70(1):41-55.
Rubin, Comment: Neyman (1923) and causal inference in experiments and observational studies. Statistical Science. 1990;5(4):472-480.

(56) References Cited

OTHER PUBLICATIONS

Rubin, Estimating causal effects of treatments in randomized and nonrandomized studies. Journal of Educational Psychology. 1974;66(5):688-701.
Rubin, Randomization analysis of experimental data: The Fisher randomization test comment. Journal of the American statistical association. 1980;75(371):591-593.
Salinas et al., DeepAR: Probabilistic forecasting with autoregressive recurrent networks. International Journal of Forecasting. 2019; 36(2020):1181-1191.
Santa Mina et al., Effect of total-body prehabilitation on postoperative outcomes: a systematic review and meta-analysis. Physiotherapy. 2014; 100(3):196-207.
Savje, Average treatment effects in the presence of unknown interference. The Annals of Statistics. 2021;49(2):673-701.
Schmid, Marginal and dynamic regression models for longitudinal data. Statistics in Medicine. 2001;20(21):3295-3311.
Schork, Personalized medicine: Time for one-person trials. Nature. 2015;520(7549):609-611.
Senn, Mastering variation: variance components and personalised medicine 2016;35(7):966-977.
Shamseer et al., Consort extension for reporting N-of-1 trials (CENT) 2015: Explanation and elaboration. Journal of Clinical Epidemiology. 2016;76:18-46.
Shapiro et al., Characterizing COVID-19 and influenza illnesses in the real world via person-generated health data. Patterns (NY). 2020; 2(1):100188 pp. 1-14.
Shi et al., A rare mutation of /31-adrenergic receptor affects sleep/wake behaviors. Neuron. 2019;103(6):1044-1055.
Shillan et al., Use of Machine Learning to Analyse Routinely Collected Intensive Care Unit Data: A Systematic Review. Crit Care. 2019; 23(1):284, pp. 1-11.
Soleimani etal., Treatment-response models for counterfactual reasoning with continuous-time, continuous-valued interventions. arXiv preprint arXiv:1704.02038. 2017; pp. 1-11.
Stevens-Lapsley et al., Comparison of self-reported knee injury and osteoarthritis outcome score to performance measures in patients after total knee arthroplasty. PM R. 2011; 3(6):541-549.
Su et al., Improve postoperative sleep: what can we do? Curr Opin Anaesthesiol. Feb. 2018;31(1):83-88.
Suo et al., GLIMA: Global and Local Time Series Imputation with Multi-directional Attention Learning. 2020 IEEE International Conference on Big Data (Big Data), Atlanta, GA, USA. 2020; pp. 798-807.
Tomakv et al., A clinically applicable approach to continuous prediction of future acute kidney injury. Nature. 2019; 572(7767):116-119.
Unknown, Estimated Influenza Illnesses, Medical visits, Hospitalizations, and Deaths in the United States—2018-2019 influenza season. CDC. 2020; 5 pages. Available at https://web.archive.org/web/20200128214342/https://www.cdc.gov/flu/about/burden/2018-2019.html.
U.S. Appl. No. 16/926,510 Non-Final Office Action dated Jul. 20, 2023.
U.S. Appl. No. 16/926,510 Notice of Allowance dated Mar. 13, 2024.
Van Calster et al., Calibration: the Achilles heel of predictive analytics. BMC Med. 2019;17(1):230, pp. 1-7.
Van Den Oord et al., Pixel recurrent neural networks. Proceedings of the 33rd International Conference on Machine Learning, New York, NY, USA. 2016; 48:1747-1756. Available at https://arxiv.org/abs/1601.06759v3 (10 pages).
Van Den Oord et al., Wavenet: A generative model for raw audio. arXivpreprint arXiv: 1609.03499. 2016, pp. 1-15.
Vanderweele et al., Directed acyclic graphs, sufficient causes, and the properties of conditioning on a common effect. Am J Epidemiol. 2007; 166(9):1096-1104.
Vaswani et al., Attention is all you need. NeurIPS Proceedings. Advances in Neural Information Processing Systems 30 (NIPS 2017). 2017; 11 pages. Available at https://papers.nips.cc/paper_files/paper/2017/hash/3f5ee243547dee91fbd053c1c4a845aa-Abstract.html.
Viboud et al., Fitbit-informed influenza forecasts. Lancet Digit Health. 2020; 2(2):e54-e55.
Vieira et al., Dynamic modelling of n-of-1 data: powerful and flexible data analytics applied to individualised studies. Health Psychology Review. 2017;11(3):222-234.
Vohra et al., Consort extension for reporting N-of-1 trials (CENT) 2015 Statement. Journal of Clinical Epidemiology. 2016;76:9-17.
Wang, Causal Inference under Temporal and Spatial Interference. arXiv:2106.15074 [stat.ME]. 2021; 57 pages.
Yang Y., Consistency of cross validation for comparing regression procedures. The Annals of Statistics. 2007;35(6):2450-2473.
Zeileis et al., strucchange: An R Package for Testing for Structural Change in Linear Regression Models. J Stat Softw. 2002; 7(2):1-38.
Zucker et al., Combining single patient (N-of-1) trials to estimate population treatment effects and to evaluate individual patient responses to treatment. J Clin Epidemiol. 1997;50(4):401-410.
Zucker, Individual (N-of-1) trials can be combined to give population comparative treatment effect estimates: methodologic considerations. J Clin Epidemiol. 2010;63(12):1312-1323.

\* cited by examiner

SENSOR-BASED MACHINE LEARNING IN A HEALTH PREDICTION ENVIRONMENT

CROSS REFERENCE TO RELATED APPLICATIONS

This application is a continuation-in-part of U.S. patent application Ser. No. 16/953,256, filed Nov. 19, 2020, which is a continuation of U.S. patent application Ser. No. 14/977,194, filed Dec. 21, 2015, now abandoned, each of which are incorporated by reference herein in their entirety.

TECHNICAL FIELD

This document generally describes technology related to computer-based dynamic phenotyping of medical and/or behavioral data, such as activity tracker data for the purpose of characterizing an individual's health.

BACKGROUND

Medical and behavioral data includes data that provides insights into a person's health and wellness (e.g., fitness level, medical conditions, health behavior). Medical and behavioral data is generated from a variety of different sources, such as mobile computing devices (e.g., smartphones), activity trackers (e.g., digital pedometers, heart rate monitors), wearable devices (e.g., smart watches, smart clothing), electronic scales (e.g., Wi-Fi scales), medical records (e.g., electronic medical records (EMR) systems), user-logged information (e.g., online food diary, activity log), and/or medical device information (e.g., data generated by an individual's medical devices). Such data sources, whether alone or in combination, can provide medical and behavioral data on an individual (a person or user) as large sets of temporally dense, multi-scale event streams. For example, an individual may have a Wi-Fi scale to measure body weight, an online food diary to record his/her diet, and a digital pedometer (e.g., FITBIT device) to record physical activity at a minute-by-minute granularity. In each of these examples data sources can provide an event stream of medical and behavioral data for the individual, such as daily weigh-in information, food and beverages consumed across meals, and numbers of steps taken during time intervals throughout each day.

SUMMARY

This document generally describes computer-based technology for analyzing medical and behavioral data from a variety of different data sources, such as wearable devices, activity trackers, mobile computing devices, medical data (e.g., EMR, lab data), and/or user-logged information, to determine a variety of information regarding an individual's health. For example, newer forms of behavioral and activity data, such as those generated by wearable devices and activity trackers, can be combined with more traditional medical data sources, such as medical claims, EMR, and lab data, to predict an individual's health risks in a more timely and accurate fashion, and to determine more appropriate and effective interventions to prevent or mitigate health risks.

In one implementation, a computer-implemented method includes accessing, by a computer system, behavior data for an individual (a person or user), the behavior data includes one or more time series of events indicating health-related behaviors of the individual; determining, by the computer system, a behavior score for the individual based on the behavior data, the behavior score indicates a latent behavior state for the individual; augmenting, by the computer system, the behavioral score with medical data for the individual; identifying, by the computer system, a health-behavior phenotype for the individual based, at least in part, on a current position or trajectory of the augmented behavioral score within a latent health-behavior space, the latent health-behavior space correlates the individual's augmented behavioral score with the health-behavior phenotype for the individual; assigning, by the computer system, the individual to a particular population segment from among a plurality of population segments based, at least in part, on the current position or trajectory of the individual within the latent health-behavior space; and outputting, by the computer system, information that identifies the particular population segment in association with the individual.

Such a computer-implemented method can optionally include one or more of the following features. The behavior data can include data from one or more of: an activity tracking device that is associated with the individual, smart clothing with embedded sensors, wireless scale that provides weight measurements, mobile applications running on one or more mobile devices associated with the individual, an electronic dietary log associated with the individual, glucose meters, blood pressure monitors, heart rate monitors, heart rate variability monitors, and other health-related sensors. The behavior score can include an adherence behavior score that indicates how compliant the individual is with regard to a schedule or policy. The behavior score can include a consistency behavior score that indicates consistency of the individual with regard to following a schedule or policy. The behavior score can include a goal orientedness behavior score that indicates how well the individual completes goals that are set for the individual. The behavior score can include an activity level behavior score that indicates how physically active an individual is across one or more measured activities. The behavior score can include a receptivity behavior score that indicates how an extent to which the individual responds positively to messages or interventions to promote a healthier lifestyle. The behavior score can include a responsiveness behavior score that indicates how rapidly the individual responds to messages or interventions to promote a healthier lifestyle. The behavior score can include a habit formation behavior score that indicates a duration over which the individual changes his/her behavior in response to messages or interventions to promote a healthier lifestyle.

The computer-implemented method can further include accessing, by the computer system, the medical data for the individual that indicates one or more health conditions of the individual; determining, by the computer system, the latent health state for the individual based, at least in part, on the medical data, wherein the behavioral score is augmented based on the determined latent health state for the individual. The medical data can include one or more of: lab data for the individual, electronic medical records for the individual, and clinical data for the individual. The identifying can also include identifying a trajectory within the latent health-behavior space for the individual. The particular population segment can be assigned for the individual based additionally on the identified trajectory within the latent health-behavior space. The trajectory can include a shape or trajectory of the individual's position within the latent health-behavior space over a period of time. The period of time can include a rolling window of time that extends from a current time back a threshold length of time.

The latent health-behavior space can include at least one medical-related dimension and at least one behavior-related dimension. The medical-related dimension can include one or more of: a future medical cost dimension that indicates a projected future medical cost for individuals, a sleep-related fatigue dimension that indicates levels of fatigue resulting from a lack of sleep, a risk of illness dimension that indicates a risk of contracting an illness within a threshold period of time, and a disease progression dimension that indicates a stage of a disease. The behavior-related dimension can include one or more of: a lifestyle healthiness dimension that indicates a level of lifestyle healthiness for an individual, a circadian rhythm disruption dimension that indicates a level at which an individual's circadian rhythm is disrupted, an immune system response dimension that indicates how well an individual's immune system fends off and recovers from illness, a mobility dimension that indicates a level of mobility for an individual, and a persuadability dimension that indicates how well an individual follows health-related direction to improve healthiness.

The computer-implemented method can further include determining, by the computer system, one or more interventions for the individual based, at least in part, on the particular population segment assigned to the individual; and outputting, by the computer system, information that identifies the one or more interventions.

In another implementation, a computer system includes: one or more processors; and one or more storage devices storing instructions that, when executed, cause the one or more processors to perform operations including: accessing behavior data for an individual, wherein the behavior data includes one or more time series of events indicating health-related behaviors of the individual; determining a behavior score for the individual based on the behavior data, wherein the behavior score indicates a latent behavior state for the individual; augmenting the behavioral score with medical data for the individual; identifying a health-behavior phenotype for the individual based, at least in part, on a current position or trajectory of the augmented behavioral score within a latent health-behavior space, wherein the latent health-behavior space correlates the individual's augmented behavioral score with the health-behavior phenotype for the individual; assigning the individual to a particular population segment from among a plurality of population segments based, at least in part, on the current position or trajectory of the individual within the latent health-behavior space; and outputting information that identifies the particular population segment in association with the individual.

Certain implementations may provide one or more advantages. For example, behavioral scores, such as indexes measuring an individual's pattern of interacting with the external world (e.g., adherence to a schedule, likelihood to exercise), can be used to proactively identify symptoms of medical conditions before they arise. For instance, minute-based pedometer data (steps taken every minute) can be used to identify nighttime activity that could be caused by nocturia (frequent urination at night) or, when combined with minute-level sleep actigraphy, can be used to identify sleep apnea (pauses in breathing during sleep, often accompanied by short arousals and movement), circadian rhythm disorders, and/or restless leg syndrome. In another example, Influenza can be identified by a decrease in the level of activity as measured by pedometers and workout trackers. In a similar fashion, the evolution of exercise and activity pattern over time may be used to characterize the progression of neurodegenerative diseases. Mobility patterns as sourced by activity trackers can also be employed to detect acute episodes of depression and isolation or maniac events. Activity trackers can provide mobility and wellbeing information for individuals during hospitalization (e.g., to assess if their circadian rhythm is disrupted) or immediately after it (e.g., to assess if a minimum level of exercise to is performed, to decrease the risk of readmissions). In a further example, the increase of weight (leading to obesity) can be predicted by analyzing the caloric intake in food diaries.

In another example, an individual's behavioral scores and medical data can be used to model an individual health/behavior latent state (e.g., current position of the individual within a space that combines medical dimensions with behavior dimensions to derive a more complete and accurate assessment of the individual's overall health/wellness), and their trajectories in the latent health/behavior space (e.g., historical changes in position within a space combining medical dimensions with behavior dimensions to better infer the individual's trajectory and future health/wellness) can be used to identify patterns that relate change in behavior with change in underlying medical conditions. The patterns that are identified in these spaces can be collectively called (health/behavior) "phenotypes" and can be used to devise behavioral therapies, to attain improvements in an individual's health outcome metrics (e.g., medical and pharmaceutical costs, healthcare utilization, etc.) or to assess eligibility for clinical trials.

In a further example, individuals, can be clustered in different segments based on, for example, their current health/behavior latent state and/or their trajectory in the latent health/behavior space. Segments can define cohorts of individuals who exhibit similarities (e.g., similar latent states, similar trajectory pattern through a latent health/behavior space) and can be used for a variety of purposes, such as to conduct studies and/or effectively deploy interventions. Such segments can dynamically vary over time. For example, different risk levels can be associated to different dynamic segments (i.e., segments that dynamically vary over time). Each segment can be prioritized in a different way with increasingly more effective (although more expensive) interventions. In addition, different segments can receive different kind of treatments. For instance, incentives can then be allocated to different segments of members identified by risk and likelihood in order to maximize overall outcome.

In another example, technical problems can be solved and/or computing performance can be improved. For instance, technical problems abound regarding large quantities of data, which may be popularly referred to as "big data," including how to process and make sense from such large data sets. Medical data (e.g., EMR, lab data) and behavior data (e.g., activity tracker data, food diaries) amount to vast quantities of data in the aggregate and for individuals. Behavior score determining provides a way to more efficiently process, combine, and determine reliable behavior metrics for individuals-which can be more efficient than other computer-based techniques that may involve more computationally intensive (and potentially less accurate techniques). Additionally, using health/behavior spaces to combine medical and behavioral information can allow for inferences into an individual's current and projected future health/wellness to be more efficiently determined.

In an aspect, a method is disclosed. The method comprises accessing, by a machine learning prediction system, a set of training data for a plurality of users of a population, the training data representative of physical statistics and symptoms for the plurality of users for each of a plurality of time periods. The method also comprises training, by the machine learning prediction system, a machine learned model using the accessed set of training data, the machine learned model configured to predict, for a first acute health condition, acute health condition onset for a user based on physical statistics of the user. The method also comprises receiving, from a target user, physical statistics data for the target user. The method also comprises determining, by the machine learning prediction system, a probability of acute health condition onset for the user within a subsequent interval of time by applying the trained machine learned model to the received physical statistics data for the target user. Finally, the method comprises, in response to the determined probability of acute health condition onset for the user exceeding a threshold, performing one or more intervention actions on behalf of the target user. In some embodiments, the one or more intervention actions comprise modifying an interface displayed by a user device of the target user to display a notification with information warning the target user of the acute health condition. In some embodiments, the one or more intervention actions comprise automatically sending a test kit corresponding to the acute health condition to the target user. In some embodiments, the one or more intervention actions comprise automatically scheduling a doctor's appointment with the target user without input from the target user. In some embodiments, each intervention of the one or more intervention actions is associated with a corresponding probability threshold. In some embodiments, receiving physical statistics data for the target user comprises receiving time series measurements of a set of physical statistics from a wearable health sensor of the user. In some embodiments, the set of training data further comprises acute health condition symptom data for the plurality of users. In some embodiments, the method further comprises sending, to the plurality of users, a survey requesting health condition symptom data. In some embodiments, the acute health condition is an influenza-like illness. In some embodiments, the acute health condition is COVID-19. In some embodiments, the physical statistics data comprises a measurement of a physical statistic selected from the group of resting heart rate, activity level, daily step count, and sleep time. In some embodiments, the physical statistics data comprises a measurement of a physical statistic selected from the group of respiration rate, heart rate variability, and galvanic skin response.

In an aspect, a non-transitory computer-readable storage medium is disclosed. The non-transitory computer-readable storage medium comprises instructions which, when executed by a processor, cause the processor to perform the steps of: accessing, by a machine learning prediction system, a set of training data for a plurality of users of a population, the training data representative of physical statistics and symptoms for the plurality of users for each of a plurality of time periods, training, by the machine learning prediction system, a machine learned model using the accessed set of training data, the machine learned model configured to predict, for a first acute health condition, acute health condition onset for a user based on physical statistics of the user, receiving, from a target user, physical statistics data for the target user, determining, by the machine learning prediction system, a probability of acute health condition onset for the user within a subsequent interval of time by applying the trained machine learned model to the received physical statistics data for the target user; and, in response to the determined probability of acute health condition onset for the user exceeding a threshold, performing one or more intervention actions on behalf of the target user. In some embodiments, the one or more intervention actions comprise modifying an interface displayed by a user device of the target user to display a notification with information warning the target user of the acute health condition. In some embodiments, the one or more intervention actions comprise automatically sending a test kit corresponding to the acute health condition to the target user. In some embodiments, the one or more intervention actions comprise automatically scheduling a doctor's appointment with the target user without input from the target user. In some embodiments, receiving physical statistics data for the target user comprises receiving time series measurements of a set of physical statistics from a wearable health sensor of the user. In some embodiments, the acute health condition is an influenza-like illness. In some embodiments, the physical statistics data comprises a measurement of a physical statistic selected from the group of resting heart rate, activity level, daily step count, and sleep time. In some embodiments, the physical statistics data comprises a measurement of a physical statistic selected from the group of respiration rate, heart rate variability, and galvanic skin response.

In another aspect, disclosed herein are computer-implemented methods, comprising: gathering, by one or more processors, a training set of data comprising behavior data and medical data for a population of a plurality of individuals, wherein the behavior data for an individual includes one or more time series of events representing health-related behaviors of the individual comprising data from one or more health-related sensors of the individual and wherein the medical data for an individual corresponds to medical assessments and treatment of the individual including one or more of: lab data, electronic medical records, and clinical data; training, based on the training set of data for the population, a machine-learned model configured to predict a trajectory of an individual within a latent health-behavior space, the latent health-behavior space comprising a multi-dimensional data space including a behavioral data dimension and a medical data dimension; receiving behavior data and medical data for a first individual; applying the machine-learned model to the received behavior data and medical data for the first individual; and predicting a trajectory of the first individual within the latent health-behavior space based on an output of the machine-learned model. In some embodiments, the behavior data comprises data from one or more of: an activity tracking device that is associated with the individual, smart clothing with embedded sensors, a wireless scale that provides weight measurements, mobile applications running on one or more mobile devices associated with the individual, an electronic dietary log associated with the individual, glucose meters, blood pressure monitors, heart rate monitors, and heart rate variability monitors. In some embodiments, training the machine-learned model comprises training a Markov Jump process based on the training data set. In some embodiments, the trajectory of an individual within a latent health-behavior space comprises a shape or trajectory of the individual's position within the latent health-behavior space over a period of time. In further embodiments, the period of time comprises a rolling window of time that extends from a current time back a threshold length of time. In some embodiments, the latent health-behavior space comprises at least one medical-related dimension and at least one behavior-related dimension. In further embodiments, the medical-related dimension includes one or more of: a future medical cost dimension that indicates a projected future medical cost for individuals, a sleep-related fatigue dimension that indicates levels of fatigue resulting from a lack of sleep, a risk of illness dimension that indicates a risk of contracting an illness within a threshold period of time, and a disease progression dimension that indicates a stage of a disease. In further embodiments, the behavior-related dimension includes one or more of: a lifestyle healthiness dimension that indicates a level of lifestyle healthiness for an individual, a circadian rhythm disruption dimension that indicates a level at which an individual's circadian rhythm is disrupted, an immune system response dimension that indicates how well an individual's immune system fends off and recovers from illness, a mobility dimension that indicates a level of mobility for an individual, and a persuadability dimension that indicates how well an individual follows health-related direction to improve healthiness. In some embodiments, the method further comprises: performing, by the computer system, one or more interventions for the individual based on the output of the machine learned model.

In yet another aspect, disclosed herein are non-transitory computer readable storage medium comprising instructions which, when executed by a (n) processor(s), cause the processor(s) to perform the steps of: gathering, by one or more processors, a training set of data comprising behavior data and medical data for a population of a plurality of individuals, wherein the behavior data for an individual includes one or more time series of events representing health-related behaviors of the individual comprising data from one or more health-related sensors of the individual and wherein the medical data for an individual corresponds to medical assessments and treatment of the individual including one or more of: lab data, electronic medical records, and clinical data; training, based on the training set of data for the population, a machine-learned model configured to predict a trajectory of an individual within a latent health-behavior space, the latent health-behavior space comprising a multi-dimensional data space including a behavioral data dimension and a medical data dimension; receiving behavior data and medical data for a first individual; applying the machine-learned model to the received behavior data and medical data for the first individual; and predicting a trajectory of the first individual within the latent health-behavior space based on an output of the machine-learned model. In some embodiments, the behavior data comprises data from one or more of: an activity tracking device that is associated with the individual, smart clothing with embedded sensors, a wireless scale that provides weight measurements, mobile applications running on one or more mobile devices associated with the individual, an electronic dietary log associated with the individual, glucose meters, blood pressure monitors, heart rate monitors, heart rate variability monitors, and other health-related sensors. In some embodiments, training the machine-learned model comprises training a Markov Jump process based on the training data set. In some embodiments, the trajectory an individual within a latent health-behavior space comprises a shape or trajectory of the individual's position within the latent health-behavior space over a period of time. In further embodiments, the period of time comprises a rolling window of time that extends from a current time back a threshold length of time. In some embodiments, the latent health-behavior space comprises at least one medical-related dimension and at least one behavior-related dimension. In further embodiments, the medical-related dimension includes one or more of: a future medical cost dimension that indicates a projected future medical cost for individuals, a sleep-related fatigue dimension that indicates levels of fatigue resulting from a lack of sleep, a risk of illness dimension that indicates a risk of contracting an illness within a threshold period of time, and a disease progression dimension that indicates a stage of a disease. In further embodiments, the behavior-related dimension includes one or more of: a lifestyle healthiness dimension that indicates a level of lifestyle healthiness for an individual, a circadian rhythm disruption dimension that indicates a level at which an individual's circadian rhythm is disrupted, an immune system response dimension that indicates how well an individual's immune system fends off and recovers from illness, a mobility dimension that indicates a level of mobility for an individual, and a persuadability dimension that indicates how well an individual follows health-related direction to improve healthiness. In some embodiments, the instructions, when executed by the processor(s), further cause the processor(s) to perform the steps of: determining, by the computer system, one or more interventions for the individual based on the output of the machine learned model.

In yet another aspect, disclosed herein are systems comprising: a (n) processor(s); and a non-transitory computer readable storage medium comprising instructions which, when executed by the processor(s), cause the processor(s) to perform the steps of: gathering, by one or more processors, a training set of data comprising behavior data and medical data for a population of a plurality of individuals, wherein the behavior data for an individual includes one or more time series of events representing health-related behaviors of the individual comprising data from one or more health-related sensors of the individual and wherein the medical data for an individual corresponds to medical assessments and treatment of the individual including one or more of: lab data, electronic medical records, and clinical data; training, based on the training set of data for the population, a machine-learned model configured to predict a trajectory of an individual within a latent health-behavior space, the latent health-behavior space comprising a multi-dimensional data space including a behavioral data dimension and a medical data dimension; receiving behavior data and medical data for a first individual; applying the machine-learned model to the received behavior data and medical data for the first individual; and predicting a trajectory of the first individual within the latent health-behavior space based on an output of the machine-learned model. In some embodiments, the instructions, when executed by the processor(s), further cause the processor(s) to perform the steps of: determining, by the computer system, one or more interventions for the individual based on the output of the machine learned model.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
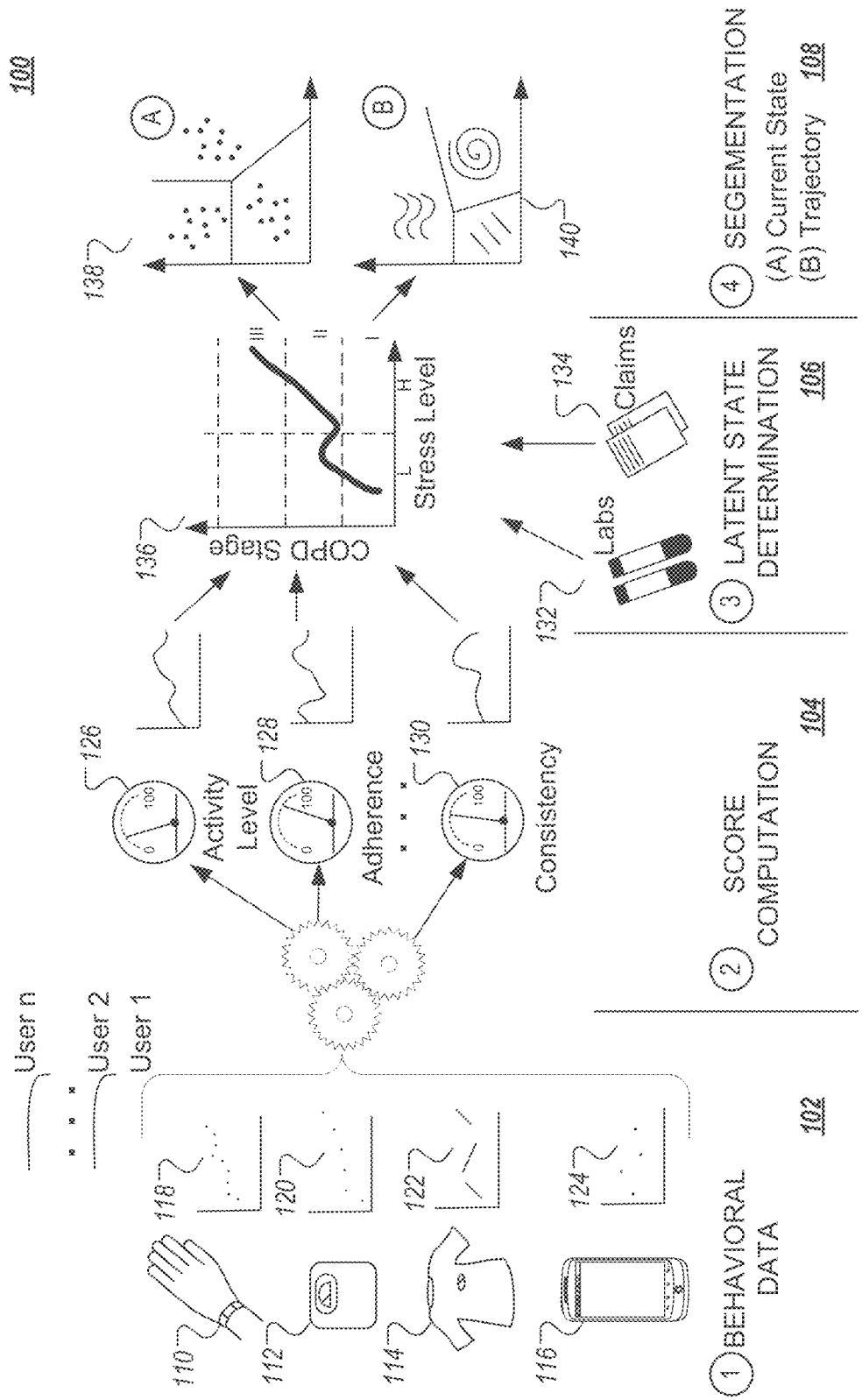
FIG. 1 is a conceptual diagram of an example computer system to perform dynamic health/behavioral phenotyping.

This document generally describes computer-based technology for combining and evaluating health data from medical and behavioral data sources to determine a variety of insights into individual health that may not be otherwise apparent or discernible from the data itself. For example, medical and behavioral data from multiple different health data sources can be combined and evaluated to determine health risks more promptly, to identify interventions that will be most effective for individuals to mitigate health risks, and/or to identify segments of individuals to whom the same or similar interventions (and/or health prescriptions) are likely to have similar effects on individual health.

For instance, a set of behavioral dimensions that capture fundamental traits of an individual's interaction with external touchpoints, such as digital health trackers, mobile devices, and healthcare services, can be identified and scored. Scores can indicate an individual's performance along various behavioral dimensions, such as adherence (i.e., the likelihood to be compliant to a schedule or a policy), receptivity (i.e., the likelihood to follow up on a request), responsiveness (i.e., the rapidity of the response), fidelity (i.e., the likelihood to stick to the same tool to measure the same activity, e.g., the same drug to treat the same condition), shareability (i.e., likelihood to share their data), consistency (i.e., likelihood to use the same tracking tools in the same manner), and/or other dimensions. Scores can vary over time for individuals, and may be determined at various timescales (e.g., minutes, hours, daily, weekly, monthly). Additionally, scores can be comparable across a population and can provide standardized metrics that can be used to identify segments of individuals who exhibit similar behavior patterns.

Scores can represent the observable outcome of a person's behavior, but their current value and variation over time can collectively be a reflection of latent health and behavioral states for individuals (i.e., their current health/behavioral phenotype). The dimensions of the hidden state space can be predetermined and can represent medical conditions (e.g., COPD disease stage) or life state (e.g., stressed). Alternatively, latent dimensions can be inferred from the data. Internal health/behavioral states can be inferred using any of a variety of appropriate techniques. For example, techniques form dynamical systems can be used to infer the trajectory of an individual in a state space that is most likely given observed scores and medical data for the individual. This can allow for individuals to be represented in the same reference state space of their health and behavior.

Inferred health/behavioral states can be used to cluster individuals into segments based on the trajectory on health/behavioral states occupied over time. This operation is referred to as "phenotyping". For example, individuals who occupy states that are the same or similar (e.g., neighboring) at a given time (e.g., they are at the same stage in the progression of a chronic disease) or have occupied similar states over time (e.g., have moved from "smoker" to "non-smoker") have a similar behavioral phenotype and can thus be grouped in the same segment. Such segments can be used in a variety of ways, such as to identify and target appropriate interventions to individuals that will have the greatest likelihood of being effective. For example, if individuals within a particular segment (e.g., individuals with irregular exercise patterns and poor diet) have been found to respond positively to some interventions (e.g., monetary incentives to exercise and/or eat healthier during periods of time when they are sedentary) but not to others (e.g., reminders on their mobile devices to exercise or eat healthier), then those interventions that have been effective (to which there has been a positive response) can be targeted to other individuals within that particular segment.

Interventions can be used to help individuals become healthier and to transition between health/behavioral states. Interventions can be varied along a number of dimensions, such as by type (e.g., motivation, incentive offer, reminder), delivery mode (e.g., text message, push notification, email), and/or time (e.g., morning, afternoon, evening, weekends, weekdays). Effective targeting of interventions across a population of diverse individuals in varied health/behavioral states can achieved by using health/behavioral states and segments to better inform the interventions that should be used for each individual.

FIG. 1 is a conceptual diagram of an example computer system 100 to generate health/behavioral phenotypes and segments. The computer system 100 can include any of a variety of appropriate computing devices, such as computer servers, cloud-based computer systems, desktop computers, mobile computing devices, and/or any combination thereof.

The example system 100 can be programmed to obtain, upon the individual's consent, behavioral data (indicated by step 102), determine scores (indicated by step 104), infer latent states (indicated by step 106), and cluster individuals into segments (indicated by step 108). For example, referring to step 102, the system 100 can collect, upon the individual's authorization, behavioral signals from various devices, such as wearable sensors 110 (e.g., activity trackers), measuring devices 112 (e.g., Wi-Fi scales), smart clothing 114 (e.g., clothing with embedded sensors), mobile applications 116 (e.g., applications running in the foreground and/or background on mobile computing devices, such as smart phones), vehicles, other computer systems (e.g., cloud-based food diary system, interactions with websites), and/or other behavioral data sources. Each of these data sources can provide time series data that represents various health-related interactions by an individual. Examples time series data 118-124 are depicted as corresponding to the data sources 110-116, respectively. As indicated by the example time series data 118-124, the time series data can vary from source to source in terms of frequency and scale. For example, an activity tracker (example wearable device 110) may provide data on an individual's activity (example interaction) every second (example regular frequency) that indicates a number of steps taken by the individual (example scale), as indicated by time series data 118. A Wi-Fi scale (example measuring device 112) may provide data that indicates an individual's weight (example scale) every time the individual weighs himself/herself (example variable frequency), as indicated by time series data 120. The behavioral data can be collected by the system 100 for a plurality of different individuals (e.g., individual 1-n) upon their authorization, each of which may have a different collection of behavioral data sources.

The computer system 100 can aggregate signals from behavior data sources and can use them to determine behavior scores, as indicated by step 104. Behavior scores can be determined based on usage pattern on any kind of repeated interaction of an individual with resources and/or services. Each type of interaction can be represented as a time series—a sequence of labeled events. Event streams can be unions of measured interactions, and can be represented using the following labeled time series:

$$T = <t_i, K_i, V_i> \qquad (1)$$

where $t_i$ is a timestamp, $K_i$ is the kind of event (e.g., daily step count, medication taken, food diary entry), and $V_i$ is a value associated with the reported event (e.g., the number of steps reported, the kind of medication taken).

A variety of different behavioral scores can be determined. Each behavioral score can be determined based on time series events streams from one or more data sources (e.g., based on combinations of data from multiple data sources). Behavioral scores can change over time and can be determined iteratively by the computer system 100 (e.g., determined every second, minute, hour, day). Some behavioral scores may be determined more frequently than other behavioral scores. For example, the frequency with which behavioral scores the computer system 100 may determine particular behavioral scores can be based on the historical volatility of the scores being determined (e.g., scores that are more volatile may be determined more frequently).

Example behavioral scores are described with regard to FIGS. 2-7, which are flowcharts of techniques for determining various behavioral scores. These example techniques can be performed by any of a variety of appropriate computer systems, such as the computer system 100. The behavioral scores can be determined as a function of the labeled time series event stream, such as from the data sources 110-116. Example behavioral scores 126-130 for activity level, adherence, and consistency are depicted in the example in FIG. 1. Additional and/or alternative techniques to determine behavioral scores can also be used, such as machine learning techniques (described in more detail below).

FIGS. 2A-2D are flowcharts of example techniques 200, 220, 250, and 280 for determining adherence scores, which are example behavioral scores that indicate how compliant an individual is with regard to a schedule and/or policy.

Figure 2A:
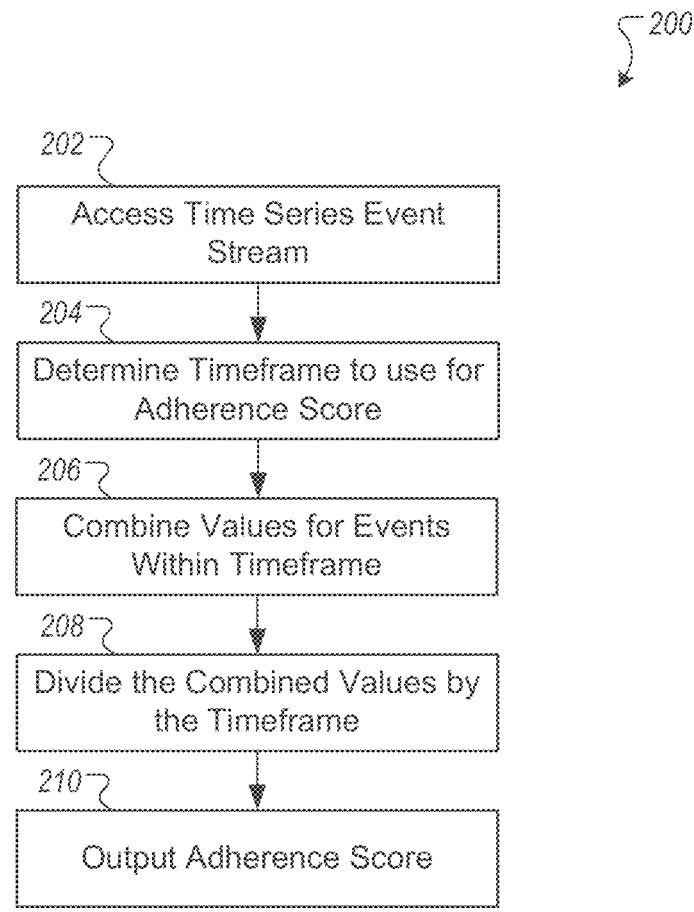
FIGS. 2A-D are flowcharts of example techniques for determining adherence scores.

Referring to FIG. 2A, the example technique 200 determines the adherence score based on an average of the values for the events over a timeframe. For example, when the policy is a medication refill policy, each event can be a medication refill and the value can be the number of days that the refill contains, which can be averaged over the timeframe during which the refills were obtained. The example technique 200 includes accessing a time series event stream (202), such as an event stream of medication refills for an individual; determining a timeframe to use for the adherence score (204); combining the values for events that fall within the timeframe (206), such as adding, multiplying, subtracting, weighting, etc.; dividing the combined values by the timeframe (208); and outputting the resulting value as the adherence score (210).

The example technique 200 can be represented by the following equation:

$$A(K) = \frac{\sum_i V_i}{t_e - t_b} \qquad (2)$$

where for the subset of T for which $K_i = K$ represent an event (e.g., medication refill for a specific drug), $V_i$ is the event value (e.g., the number of days that the refill contains, $t_e$ is the timestamp of the most recent event (e.g., refill), and $t_b$ is the timestamp of the least recent event.

Figure 2B:
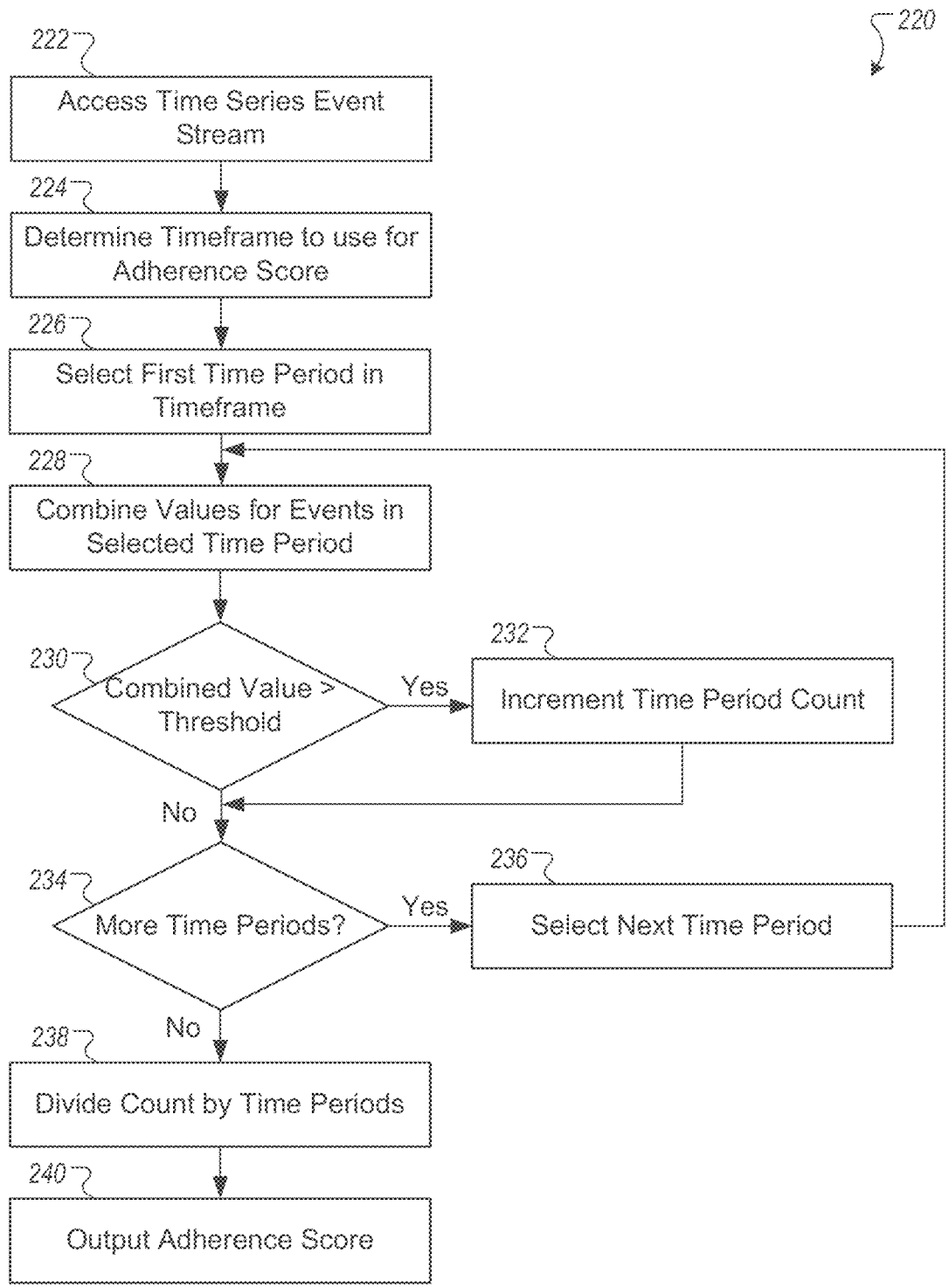

Referring to FIG. 2B, the example technique 220 determines how regularly an individual carried out an activity with a cadence represented by a time period (e.g., day, week), which can indicate an active ratio (ratio of time periods during which there was activity over all of the time periods during a timeframe). The example technique 220 includes accessing a time series event stream (222); determining a timeframe to use for the adherence score (224); selecting a first time period in the timeframe (226); and combining values for events that fall within the selected time period (228). If the combined values are greater than (or equal to) a threshold value (230), then that time period can be considered to be "active" and the time period count keeping track of active time periods can be incremented (232). If there are more time periods (234), then the next time period can be selected (236) and the steps 228-236 can be repeated. If there are no more time periods, then the count can be divided by the overall number of time periods to determine the active ratio (238) and can be output as the adherence score (240).

The example technique 220 can be represented by the following equation:

$$A(K) = \frac{P_a}{(t_e - t_b)/P} \qquad (3)$$

where P is the unit time period, $P_a$ is the number of active periods, or the periods $(t_e - t_b)/P$ for which $\Sigma_i V_i$ is larger than a certain threshold.

Figure 2C:
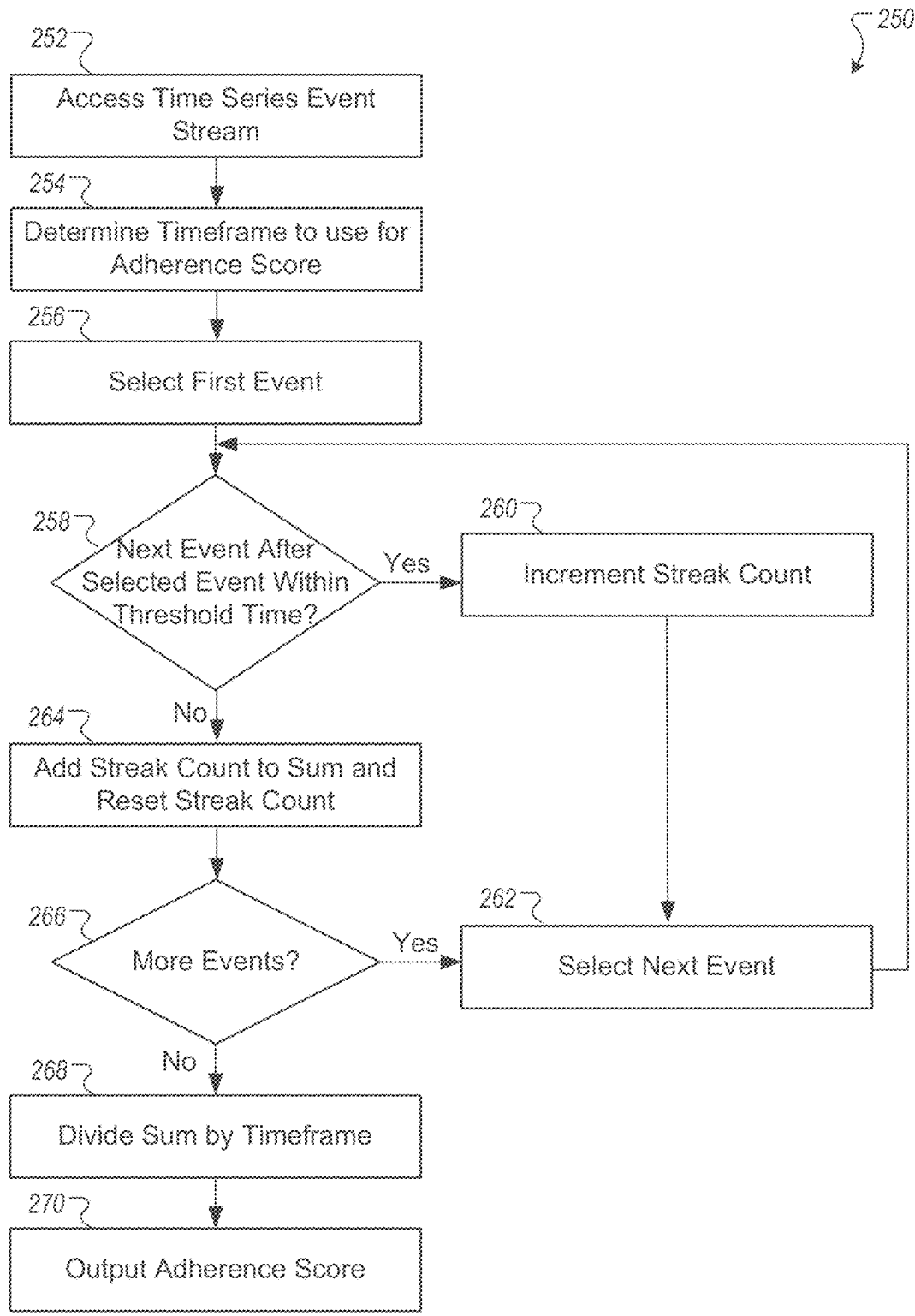

Referring to FIG. 2C, the example technique 250 determines an adherence score based on active streaks between events. The technique 250 includes accessing a time series event stream (252), determining a timeframe to use for adherence scores (254), selecting a first event during the timeframe (256), and determining whether a next event after the selected event is within a threshold time period (258). If the next event is within the threshold time period, then the selected and next event can be determined to be part of a qualifying streak and a streak counter can be incremented (260). A next event can be selected (262) and the steps 258-262 can be repeated. If a next event is not within the threshold period of time (258), then the streak count can be added to a sum and the streak count can be reset (264). If there are more events (266), then the steps 256-266 can be repeated. If there are no more events, then the sum can be divided by the timeframe (268) and output as the adherence score (270).

The example technique 250 can be represented by the following equation:

$$A(K) = \frac{\sum_j S_j}{(t_e - t_b)} \qquad (4)$$

where an active streak $S_j$ is defined as the longest time series such that no two consecutive activities are temporally separated by a period longer than $t_{gap}$, and $t_{gap}$ can be, for example, a population constant or a value learned on a per-individual basis.

Figure 2D:
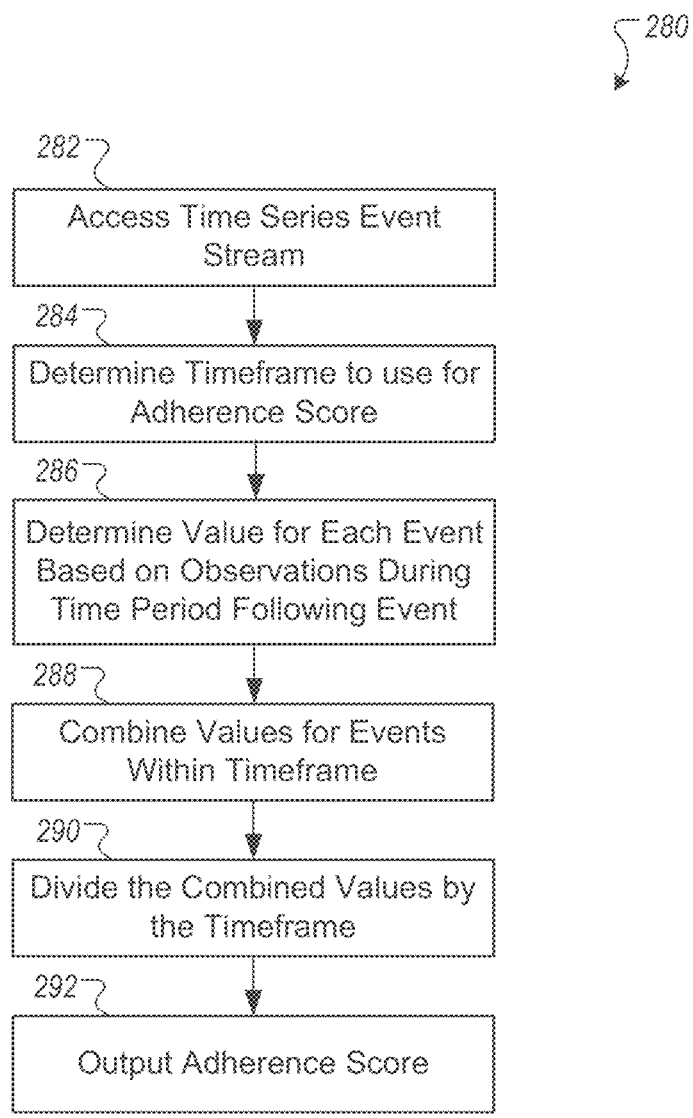

Referring to FIG. 2D, the example technique 280 can be used to determine an adherence score where the benefits of the activity can persist for a period of time after the activity has been performed. In the example technique 280, a time series event stream can be accessed (282), a timeframe to use for the adherence score can be determined (284), and values for each event within the timeframe can be determined based on observations during a time period following each event (286). For example, the benefits of the activity can be observed during the time period after which the activity took place and used to determine a value for the activity (example event). The values for the events can be combined (288), divided by the timeframe (290), and output as an adherence score (292).

The example technique 280 can be represented by the following equation:

$$A(K) = \frac{\sum_i V(K)_i}{t_e - t_b} \qquad (5)$$

where $V(K)_i$ is a value associated with activity type K, which is evaluated as providing benefits over a period of time P after the activity has been performed.

The example techniques for determining adherence scores can be performed separately and/or in combination with each other. Additionally, other techniques for determining adherence scores can also be used.

Figure 3A:
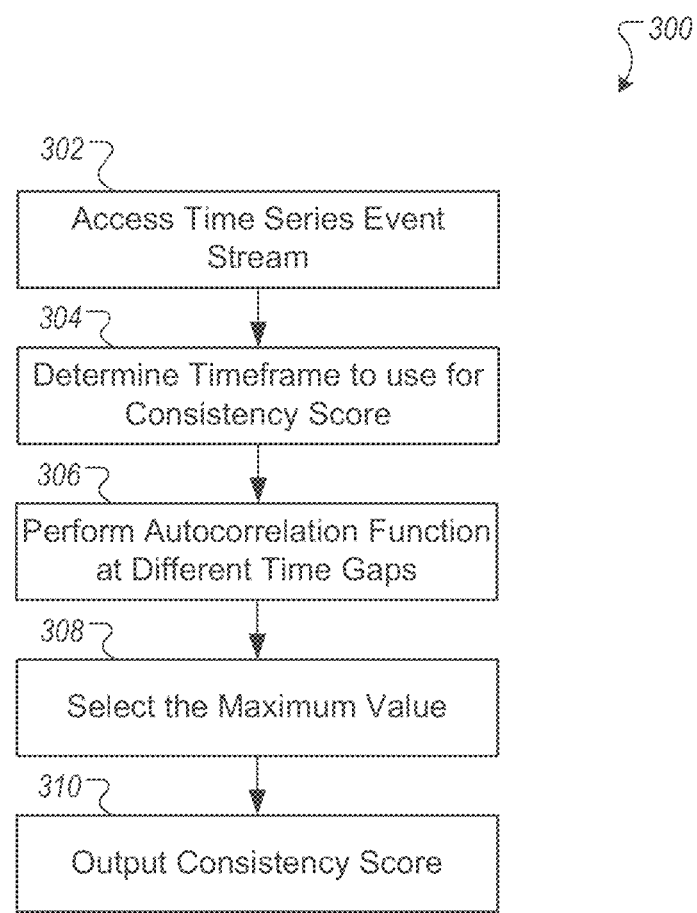
FIGS. 3A-C are flowcharts of example techniques for determining consistency scores.
Figure 3B:
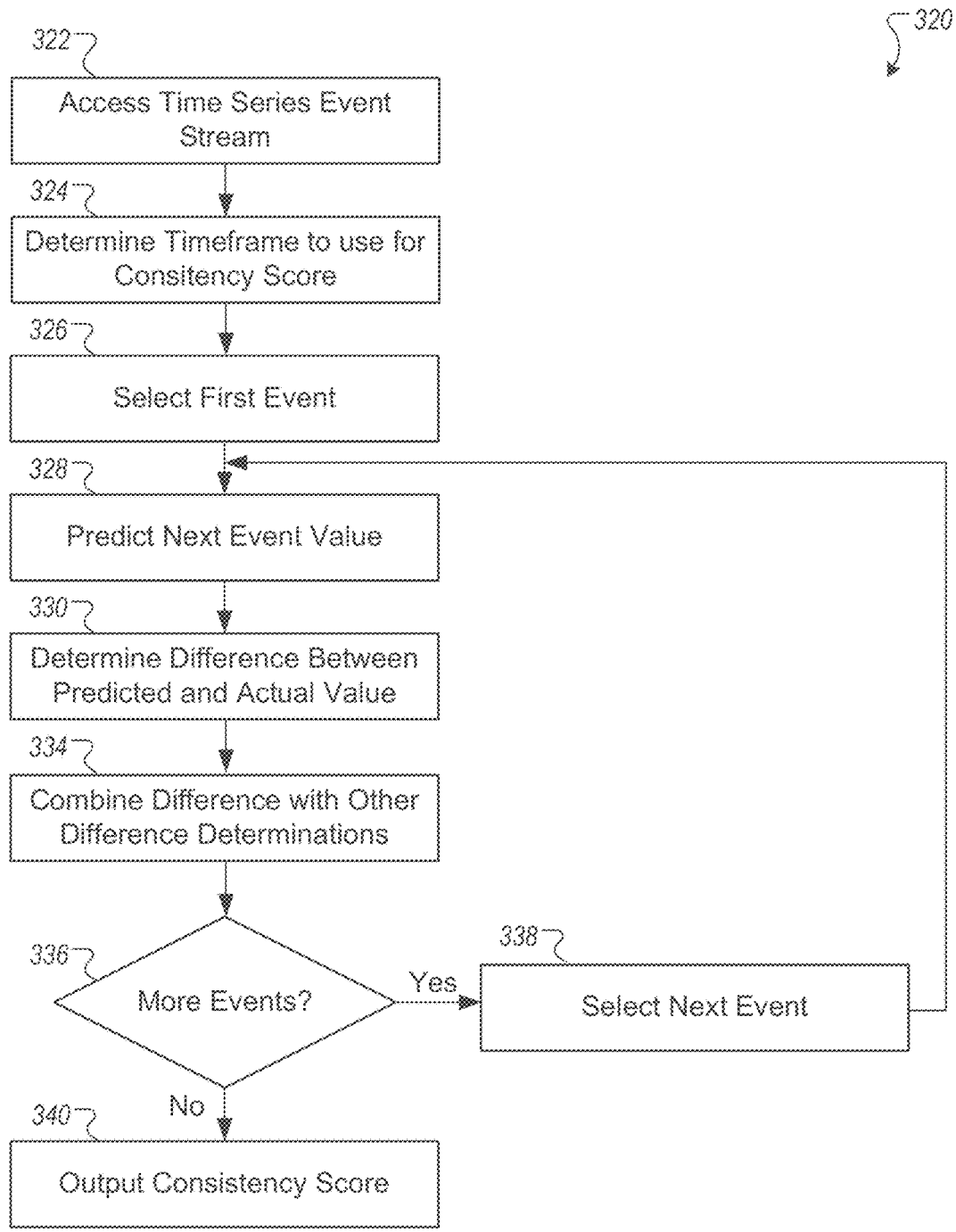
Figure 3C:
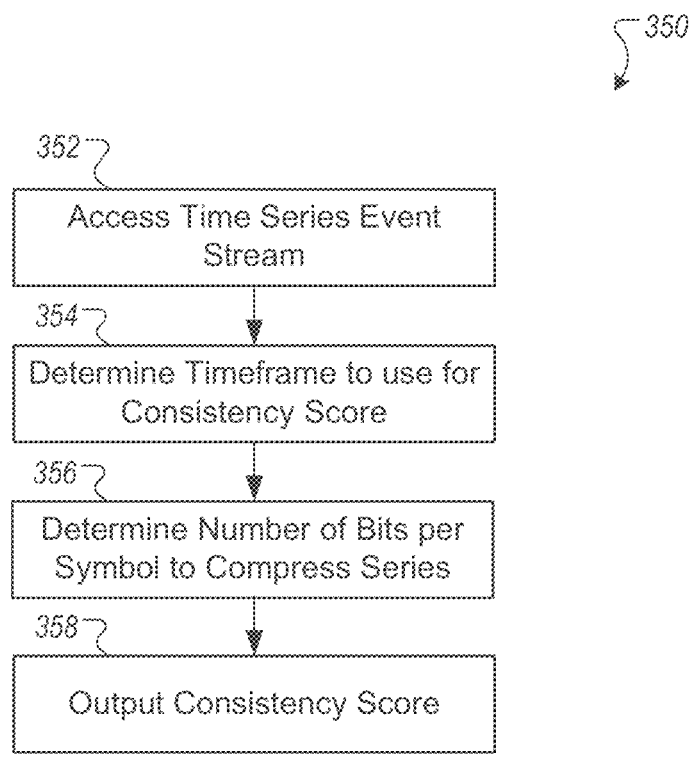

FIGS. 3A-3C are flowcharts of example techniques 300, 320, and 350 for determining consistency scores, which are example behavioral scores that indicate the consistency of an individual with a generic "regular" schedule or predefined policy, that, unlike adherence scores, may or may not be imposed by an external entity.

Referring to FIG. 3A, a first example technique 300 for determining consistency scores is presented for determining the score based on the autocorrelation function of the time series. For example, a time series event stream can be accessed (302), a timeframe for determining the consistency score can be determined (304), and an autocorrelation function can be computed for various different time gaps (306). The values from the autocorrelation function computed at the different time lags can be compared and a maximum value can be selected (308) and output as the consistency score (310). This example technique can be represented by the following equation:

$$C(K) = \max_j ACF(j) \qquad (6)$$

where the consistency score for activity type K can be inferred from the autocorrelation function $ACF(j)$ of the activity time series at different time lags $j=1 \ldots n$.

Referring to FIG. 3B, the example technique 320 can be used to determine a consistency score based on how well on average a next event in a time series can be predicted using one or more models (e.g., predefined models, models trained on data for the individual and/or population at large, models trained on a portion of the time series data, such as a prefix of the time series data). The more closely the model can predict the next value, the more consistent the time series data can be determined to be. For example, a time series data stream can be accessed (322), a timeframe to use for determining the consistency score can be determined (324), and a first event can be selected (326). One or more models can be accessed/determined and used to predict a next event value based on the selected event (328) and a difference between the predicted and actual value of the next event can be determined (330). This difference value can be combined (e.g., averaged, summed, weighted average) with other difference values determined across the time series (334). If there are more events (336), then the next event can be selected (338) and the steps 328-338 can be repeated. If there are no more events, then the combined difference values can be output as the consistency score (340).

The example technique 340 can be represented by the following example equation, which can use a model (e.g., ARIMA model trained on a prefix of the time series) to predict a next value:

$$C(K) = E[|\hat{d}_i - d_i|] \qquad (7)$$

where the time series for activity K is predicted by a model (e.g., ARIMA model trained on a prefix of the time series), $\hat{d}_t$ is the model's (e.g., ARIMA (q)) approximation of $d_i = t_{i+1} - t_i$ as the delta time between consecutive events.

Referring to FIG. 3C, the consistency score can be determined based on an average of the information content of a time series, such as a number of bits per symbol used to compress the time series. For example, a time series event stream can be accessed (352), a timeframe for the consistency score can be determined (354), a number of bits per symbol that are used to compress the series can be determined (356), and output as a consistency score (358). The following equation represents an example of the technique 350:

$$C(K) = bps(Q(d_i)) \qquad (8)$$

where the number of bits per symbol to compress the sequence is determined using standard data compression techniques (e.g., Huffman encoding, lz78). $Q(\ )$ is an exponential quantizer (e.g., Fibonacci: $Q(x) = F_k$ iff $F_k < x \leq F_{k+1}$) used to quantize the values of $d_i = t_{i+1} - t_i$, the delta time between consecutive events.

The example techniques for determining consistency scores can be performed separately and/or in combination with each other. Additionally, other techniques for determining consistency scores can also be used.

Figure 4A:
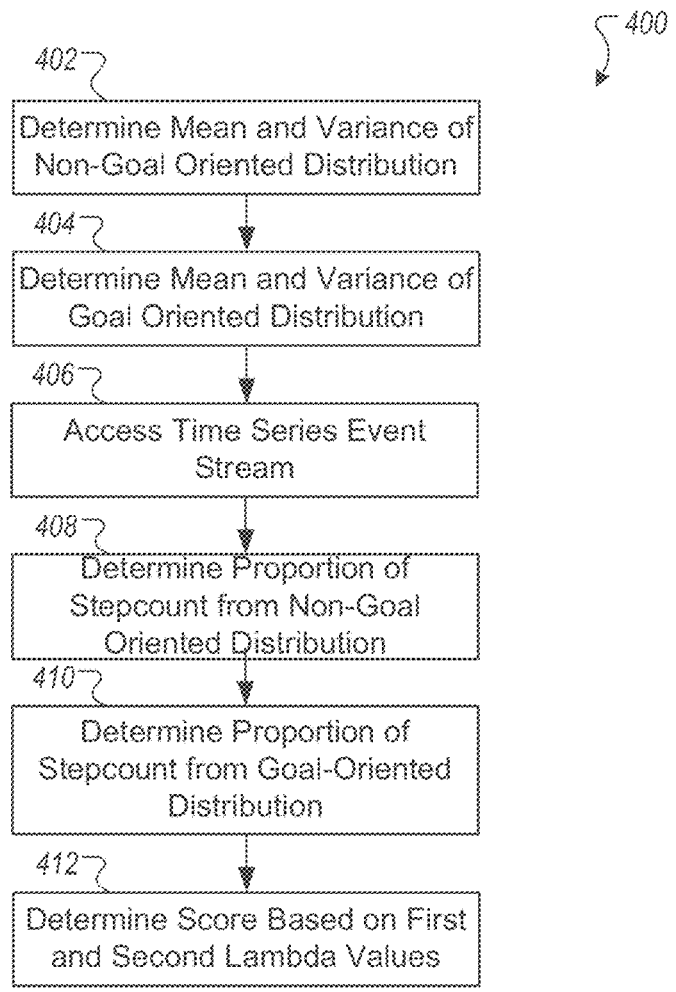
FIG. 4A is flowchart of an example technique for determining goal orientedness scores.

FIG. 4A is flowchart of an example technique 400 for determining goal orientedness scores, which are example behavioral scores that indicate how much an individual seeks to complete goals set for them, such as goal provided by a device (e.g., activity tracker) and/or mobile app. For example, FITBIT devices congratulate individuals for reaching ten thousand steps in a single day (example goal). A goal orientedness score can provide a measure of how likely an individual is to seek out this goal, and can be determined by measuring how much the individual's historical daily steps are skewed by this goal.

Figure 4B:
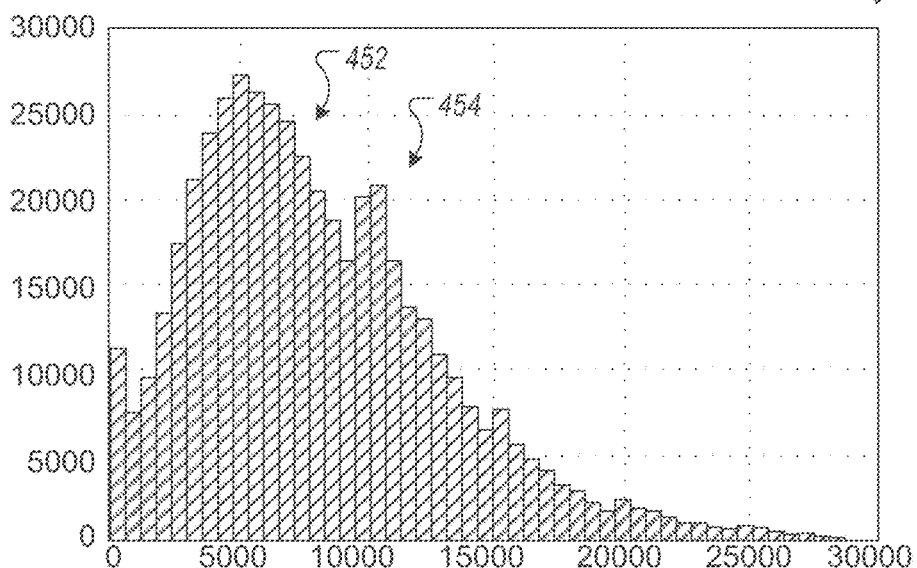
FIG. 4B is a chart that depicts an example distribution of a number of steps taken per day.

For instance, FIG. 4B is a chart 450 that depicts an example distribution of a number of steps taken per day for a population of individuals incentivized to achieve 10,000 steps/day. In this distribution, there is a first cluster 452 of events around 5,000 steps per day and a second cluster 454 of events around 10,000 steps per day, which is an example goal. Individuals that have more days with stepcount around 10,000 can be more susceptible to be goal-oriented.

The technique 400 is one example for determining goal orientedness scores and can involve comparing how much of an individual's daily stepcount events belong to a distribution concentrated around the set goal. For example, the distribution of daily stepcounts is assumed to be a mixture of two normal distributions, one non-goal-oriented, with normally distributed mean and variance that can be learned from the population (402), and one or more goal-based distributions with predetermined means for one or more specific goal sets (e.g., 10,000 steps/day) and variance normally distributed over the population. Time series data for an individual can be accessed (406) and used to estimate the proportion (lambda_1) of daily stepcounts coming from the underlying non-goal-oriented distribution (408), as well as the proportion (lambda_2) of daily stepcounts coming from the one or more goal-based distributions (410). A goal orientedness score can be determined based on the first and second lambda values (412), such as the first lambda value being divided by the second lambda value (and/or vice versa), differences between the lambda values, weighted combinations of the lambda values, and/or other combinations/comparisons of the lambda values.

The technique 400 can be represented by the following equation, which provides an example way to measure goal orientedness scores by assuming that the distribution of values V_i for activity K is represented by a mixture of two Gaussians:

$$D(V_i) = \lambda_1 N(\mu_1, \sigma_1) + \lambda_2 N(\mu_2, \sigma_2) \quad (9)$$

where parameters $\mu_1$, $\sigma_1$, $\sigma_2$ are assumed being normally distributed for the population, and $\mu_2$ is set to the specific goal set (e.g., 10,000 steps per day). Once the model is estimated, the goal orientedness score can be returned as:

$$G(K) = \lambda_1 / \lambda_2 \quad (10)$$

Figure 5:
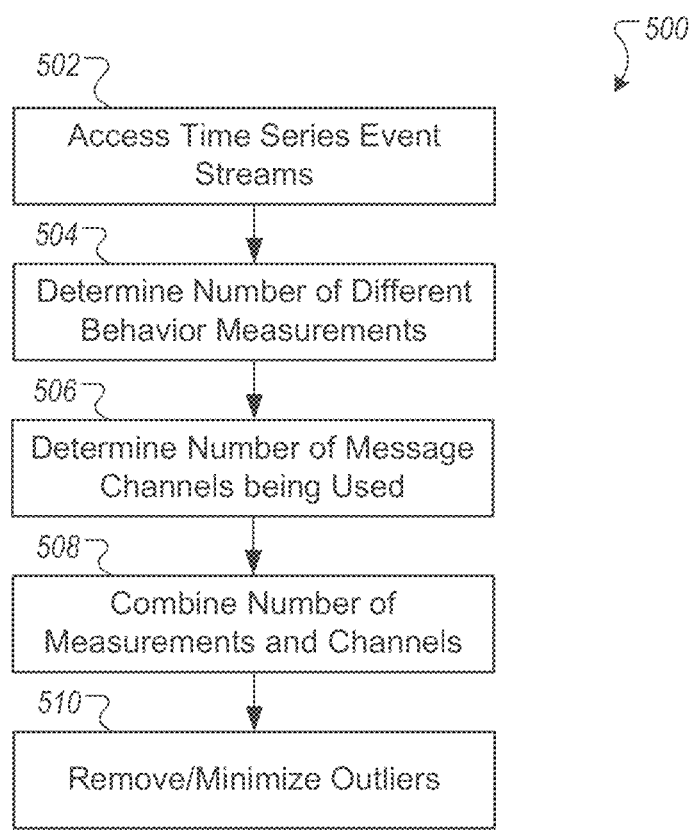
FIG. 5 is a flowchart of an example technique for determining usage variability scores.

FIG. 5 is a flowchart of an example technique 500 for determining usage variability scores, which indicate the level of differentiation of an individual across different behavior measurements (e.g., pedometers, scales, sleep monitors) and/or preferred message channels employed. For example, time series event streams can be accessed (502) and, from the event streams, a number of different sources through which activities are reported can be determined (504) and/or a number of distinct channels through which the individuals elects to receive messages can be determined (506). The number of channels and/or measurements can be combined (508) and/or outliers (e.g., values larger than the 9sth percentile) can be removed and/or minimized (510), such as by taking the logarithm of the resulting number to penalize outliers. The resulting value can be the variability score.

Figure 6:
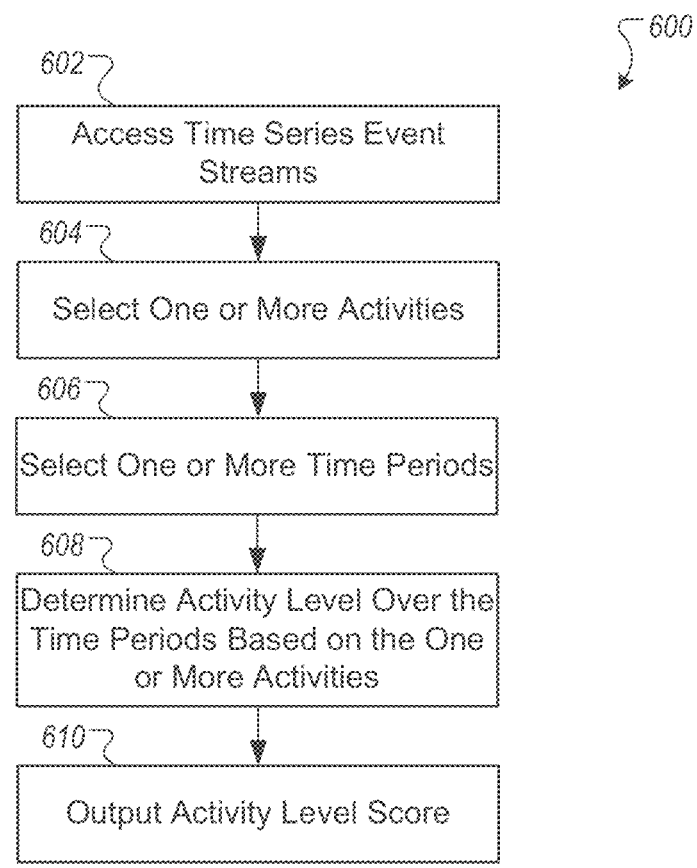
FIG. 6 is a flowchart of an example technique for determining activity level scores.

FIG. 6 is a flowchart of an example technique 600 for determining activity level scores, which can indicate how active an individual is in general. Activity level scores can be based on data from multiple activities or a single activity. Activity level scores can also be measured as the average level of activity over different time periods, such as only over active days (e.g., an active day is a day for which at least an activity has been reported) and/or over all days the individual could have been active (e.g., days of potential activity). For example, time series event streams can be accessed (602), one or more activities can be selected (604), one or more time periods can be selected (606), and an activity level over the time periods can be determined from the one or more selected activities (608). The determined activity level can be provided as the activity level score (610).

Figure 7A:
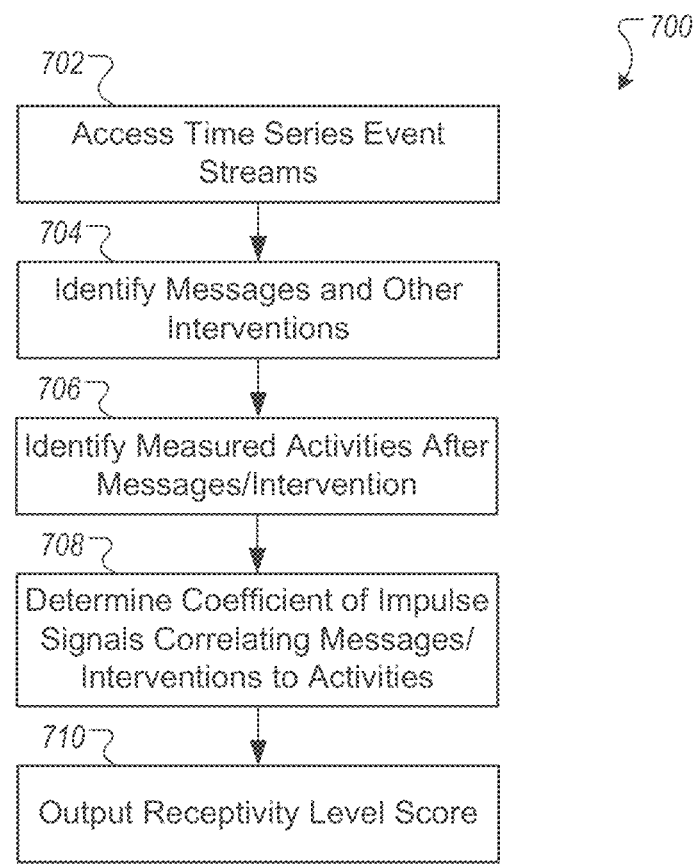
FIGS. 7A-C are flowcharts of example techniques for determining habit-formation scores.

FIGS. 7A—Care flowcharts of example techniques 700, 720, and 750 for determining habit-formation scores, which can include receptivity scores (how much an individual's behavior changes in response to a message or other intervention), responsiveness scores (how soon after receiving a message or other intervention that a change in behavior is detected), and habit formation potential scores (how long after receiving a message or other intervention a change in behavior can be expected to persist before the individual returns back to his/her pre-intervention value).

Referring to FIG. 7A, the example technique 700 determines receptivity scores, which can determine causation between messages and other interventions, and activities that the messages and/or interventions are intended to positively affect (e.g., increase activity level, improve dietary choices). For example, when an individual is sent a nudge, or a small message or encouragement meant to positively affect their behavior, how much change is seen in the affected behavior in response thereto? Is the reception of an encouragement to walk more usually followed by a noticeable increase in walked steps? Receptivity scores can indicate whether an individual is receptive to such messages/interventions.

For instance, the technique 700 includes time series event streams being accessed (702), and messages and/or other interventions that were provided to an individual being identified (704). Activities that are intended to be affected by the messages and/or other interventions and that occur after the messages and/or other interventions are provided to the individual can be identified (706). From these messages/interventions and activities, the computer system 100 can determine one or more coefficients that represent impulse signals correlating messages/interventions to the resulting activities (708). For example, the computer system 100 can calculate coefficients such as the Granger causality coefficient and/or Convergent Cross Mapping coefficient, which can indicate the causal effect of the messages/interventions on the activities. The resulting coefficient can be output as the receptivity score (710).

Figure 7B:
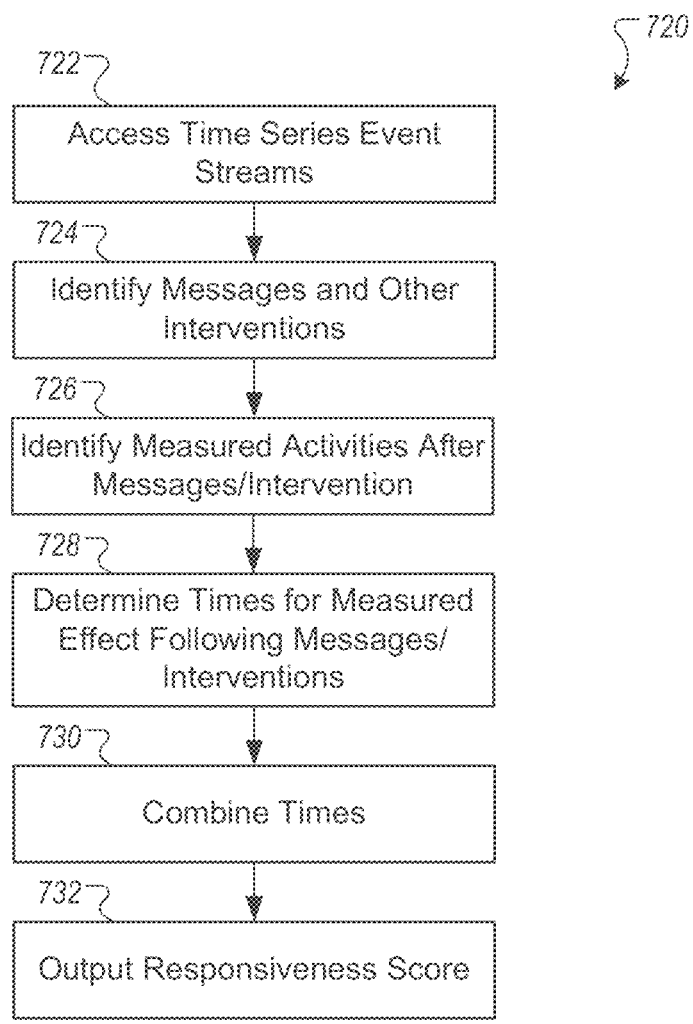

Referring to FIG. 7B, the example technique 720 can be used to determine responsiveness scores, which can indicate how quickly a change in behavior is detected from the individual following a message/intervention. For example, a responsiveness score can be based on how many days after a nudge incentivizing a person to walk more than 10,000 steps does the person actually logs 10,000 daily steps.

For instance, the technique 720 includes time series event streams being accessed (722), and messages and/or other interventions that were provided to an individual being identified (724). Activities that are intended to be affected by the messages and/or other interventions can be identified, along with the times at which they occur relative to the messages/interventions (726). The computer system 100 can determine times for the measured effects following the messages/interventions (728) and can combine the determined times (730) to generate the responsiveness score (732). For example, the computer system 100 can average the times for the individual to respond to the messages/interventions. The computer system 100 may limit performance of the technique 720 to instances when there is a measured effect size of at least E. The effect size can be one or more global constants for a population, and/or it can be learned based on the history of the individual. For example, the responsiveness score can be the inverse of the logarithm of the average time after a nudge (message/intervention) that is necessary to perceive a change in behavior measured of effect size at least E.

Figure 7C:
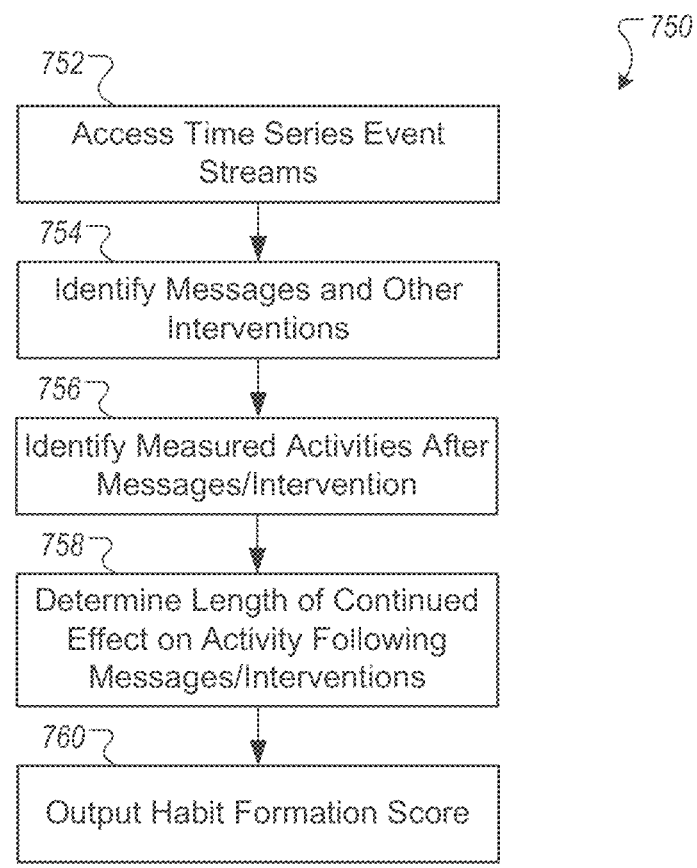

Referring to FIG. 7C, the example technique 750 can be used to determine habit formation potential scores, which can indicate how likely an individual is to keep pursuing a newly adopted behavior following a message/intervention. For example, habit formation scores can indicate how many consecutive days an individual who has been nudged will maintain a daily step count within 5% of a 10,000 daily step goal.

For instance, the technique 750 includes time series event streams being accessed (752), and messages and/or other interventions that were provided to an individual being identified (754). Activities that are intended to be affected by the messages and/or other interventions can be identified (756) and can be used to determine a length of continued effect on activity following messages/interventions (758). Such effect may be within a margin of a target/goal effect, such as being with a threshold percentage (e.g., 5%, 10%) of a target activity level. Such length may be determined based on a number of consecutive events that are within a target/goal effect. The computer system 100 can use the determination to generate the habit formation scores (760).

The computer system 100 can additionally and/or alternatively determine a variety of other behavior scores. For example, the computer system 100 can determine one or more activity-specific scores. Some activities can give rise to specific scores that are idiosyncratic to the specific activity and may not be directly generalized for other activities. One example is sleep quality scores, which can indicate how well the individual sleeps and how consistent their sleep schedule is. In case minute-level sleep data are present, sleep quality scores can be determined based on a variety of factors, such as the weighted average sleep lengths, average number of distinct sleep periods (e.g., if sleep is regularly broken during sleep period), standard deviation of nightly sleep, standard deviation of falling asleep, and/or standard deviation of waking up times.

Another behavior score that can be determined is a geographic fingerprint score, which can indicate where an individual spends their time as measured by location sources, such as GPS trackers from various devices. For example, a geographic fingerprint score can indicate whether an individual lives/works/recreates in a high cost-of-living city, in a rural area, a polluted area, etc.

Location variability scores can also be determined. Such scores can indicate how likely an individual is to be found in the same or different places. For example, a location variability score can indicate whether an individual is spending most of his/her time at home, at work, equally distributed between the two, how frequently the individual travels, or other location variation details. Location variability scores can be measured in any of a variety of ways, such as being based on the percentage of time spent within a given threshold distance (e.g., 100 yards) from one or more frequently visited geographic locations, such as a person's home or work.

Seasonality scores can additionally be determined. Seasonality scores can indicate how likely an individual is to display seasonal behavior patterns, such as weekly seasonality patterns, monthly seasonality patterns, quarterly seasonality patterns, etc. For example, seasonality scores can measure if the individual has a significant different pattern of activities during weekdays/weekend or summer/winter, such as the individual being more likely to run on weekdays rather than weekends. Seasonality scores can be determined with regard to a specific activity or to a set of activities. Seasonality scores can be measured using any of a variety of appropriate techniques, such as the top-k terms of an ACF (autocorrelation function) (to capture weekly/monthly seasonality) and time distributions (whether the activity is concentrated around days/nights, or weekdays/weekends).

The computer system 100 can also determine incentive sensitivity scores, which can estimate the marginal cost that need to be presented to the individual in order for the individual to accomplish an action, such as run an extra mile or add an extra app.

Shareability/extraversion scores can be determined and can provide a measure of how likely the individual is to share progress achieved with other individuals and to reach out to their social circle, such as through social media and/or social networks.

The computer system 100 can also determine fidelity scores, which indicate the likelihood of the individual sticking to one program, device, medication, etc., to achieve a specific purpose.

Peer sensitivity scores can also be determined and can provide a measure of a person's likelihood to be influenced by messages relayed by their social network. For example, the peer sensitivity scores can examine social network activity, such as posts, tweets, friend additions, likes, etc., to determine its effect on an individual's behavior.

The scores described above can be determined by the computer system 100 alone, together, and/or in various combinations. Such combinations of scores can be individualized for each individual, and can be tailored based on a number of factors, such as a number and type of different behavior data sources that are available to the computer system 100 for an individual. Other scores and variations of the scores above are also possible.

To be responsive to quick changes, in a time series, the scores described above may be computed only on the time window of the most recent k measurements or on all the measurements collected in a recent time interval. The current score may also be a weighted average between the windowed score and the score computed on the complete time series.

Scores can also be normalized to permit comparisons among individuals in a population. For example, a score S=S(K) can be normalized into $S_N$ by, for example, transforming it into the quantile Q(S,D(S)) on the distribution of score over all the population scores distribution D(S). The resulting normalized score, which can be readily compared across individuals in a population, can be represented as:

$$S_N = Q(S, D(S)) \quad (11)$$

Additionally and/or alternatively, the scores described above can be determined using machine learning based approaches. For example, for a given score S, event streams can qualitatively be labeled based on, for example, whether they are perceived as being a high score ($S_H$) or a low score ($S_L$). Such labelling may be automatically performed by the computer system 100 and/or can be performed with the assistance of one or more human operators. Subsequently, the computer system 100 can use train a binary classifier on the event time series to recognize labels $S_H$ and $S_L$. SVM, Ensemble methods (e.g., random forest) can be used and trained on features computed on the event streams (e.g., mean, variance, etc.). Alternatively, one can train classifier based on neural networks LSTM (long-short term memory network) or Convnets (convolutional neural networks) directly on the raw event stream. The trained classifier can then be evaluated on new individual event streams and the output probability of an event stream belonging to $S_H$ can then be used as normalized score $S_N$ for the individual.

Behavioral scores capture an individual's current state in their observed behavioral space. Scores can be a reflection of a latent, generally non-observable internal state. For example, upon entering a stressed out period at work, activity level and receptivity scores of an individual may likely decrease, whereas other scores, such as price and incentive sensitivity, can be expected to be less affected.

Figure 8:
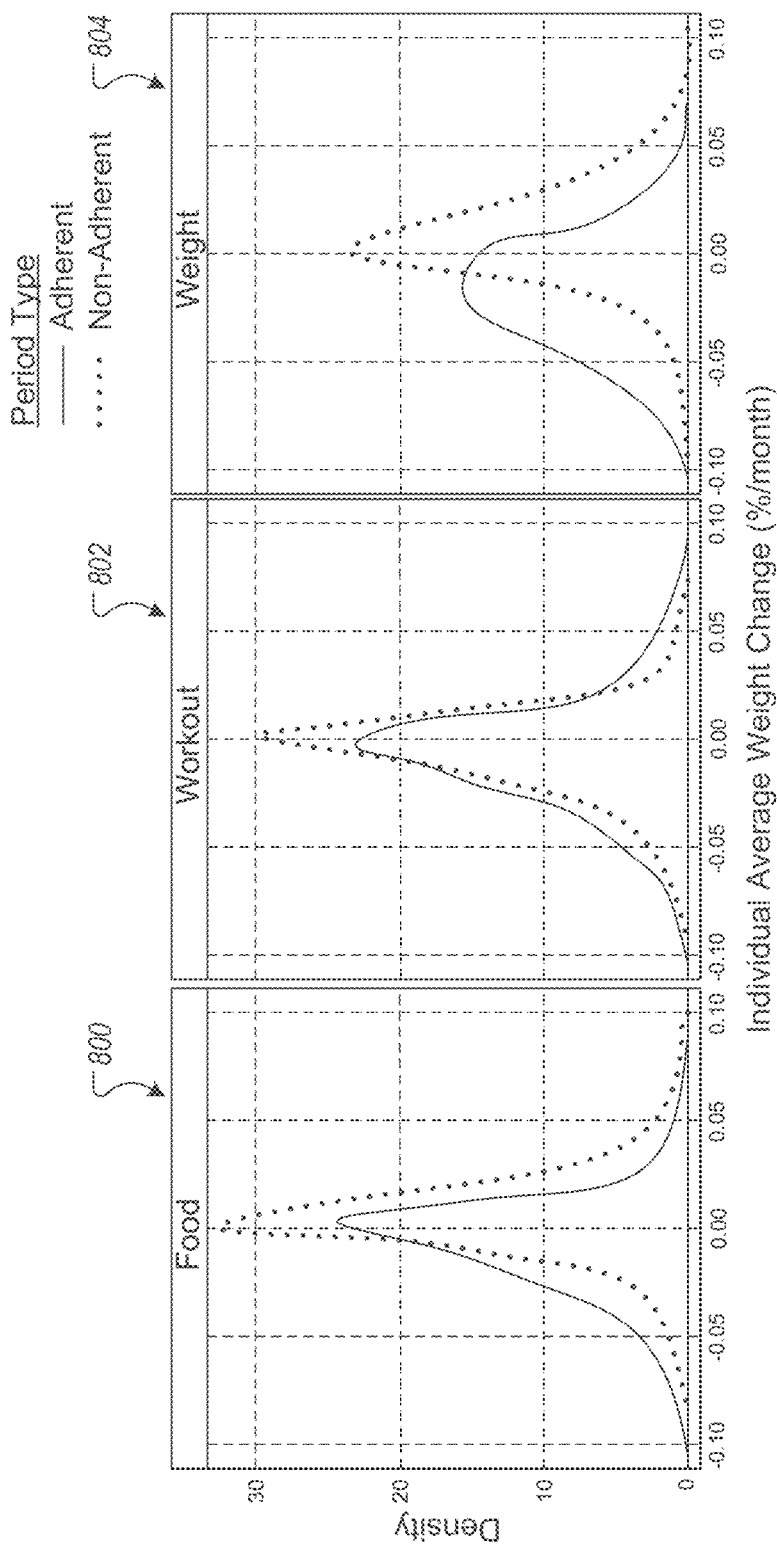
FIG. 8 depicts graphs showing example changes in consistency related to tracking activity.

In another example, as depicted in the graphs 800-804 presented in FIG. 8, a change in consistency in tracking activity (for workout, food logging, and self-weighting) is predictive of a change in body mass. For instance, the graph 800 depicts the average weight change for individuals during adherent and non-adherent periods of weight logging, the graph 802 depicts the average weight change for individuals during adherent and non-adherent periods of food logging, and the graph 804 depicts the average weight change for individuals during adherent and non-adherent periods of workout logging. Each of these graphs 800-804 indicates that non-adherence tends to increase the likelihood of weight gain.

The examples discussed above regarding entering a stressed out work period and changes to an individual's body mass can be modeled as states in a latent space of health/wellness of the individual, which can be observable in terms of changes in behavioral scores. Behavioral scores can also be affected by changes in an individual's health, that is, changes in internal states that can be directly related to health. For example, consistency, activity level, and responsiveness scores are likely to decrease as an individual's health degrades, e.g., due to the progression of a chronic condition such as COPD or CKD. Behavioral scores can allow a better explanatory power in making inferences about an individual's behavior and health latent states.

Referring back to FIG. 1, at step 106 the computer system 100 can use the behavior scores in combination with medical data to determine latent states of each individual in their health/behavior state space (latent state inference). The latent state space can be inferred based on behavioral scores, such as the example behavioral scores 126-130 for activity level, adhering, and consistency, as well as on medical data, such as lab data 132 and medical claims data 134. An example of a 2-dimensional latent state space 136 that relates an individual's COPD stage with the individual's stress level over time is depicted in FIG. 1. As depicted in this example, the latent state illuminates the progression of the individual's medical condition (progressing from COPD stage I to III) in conjunction to a change in the individual's stress level (progressing from Low to High). This behavioral latent dimension can add additional information to understand and better categorize an individual's health state, both in terms of disease states and in terms of behavioral parameters.

Hidden internal states can be identified at step 106 by combing behavioral scores with each other and/or with medical information. This leads to a model that more accurately identifies current states occupied by an individual, which can be used to better target interventions. For instance, latent state information can be used to better and more accurately cluster individuals into segments of similar individuals, which can aid in generating more effective interventions for the individuals.

An individual trajectory in a latent health space can be determined from behavioral scores by the computer system 100 through a variety of techniques, such as dynamical system techniques and machine learning techniques like Hidden Markov Models, Markov Jump Processes, and particle filters.

For example, an individual's evolution in latent health space can be modeled as a Markov Jump Process. For instance, Markov jump processes have been trained from a population of subjects with Chronic Kidney Disease (CKD) to infer the stage of the disease's progression (stage 1-V) in an unsupervised manner, such as the example disease progression model depicted in FIG. 9, which is from Wang, Xiang, et al., "Unsupervised Learning of Disease Progression Models," *KOO* '14 (Aug. 27-27, 2014, New York, NY). In the example model depicted in FIG. 9, the latent state space can be composed of a single dimension (the disease stage) S and transitions within the model can be limited to adjacent states that increase from stage to stage (decreases along stages not permitted). Transitions in the model can be triggered by the change in health, such as the insurgence of new comorbidities, as indicated by X (comorbidity variable). The likelihood of a comorbidity can be inferred by the model from the set of clinical observations, as indicated by O (e.g., diagnosis codes from claims) for example through a noisy-or network. Models can estimate the parameters from a population of individuals and to output distributions over any of a variety of stages S for each individual at any point in time. The greater the value of a current stage S[i] (stage i) for an individual, the more likely the individual is to be found at that point of the progression given the observations.

Figure 9:
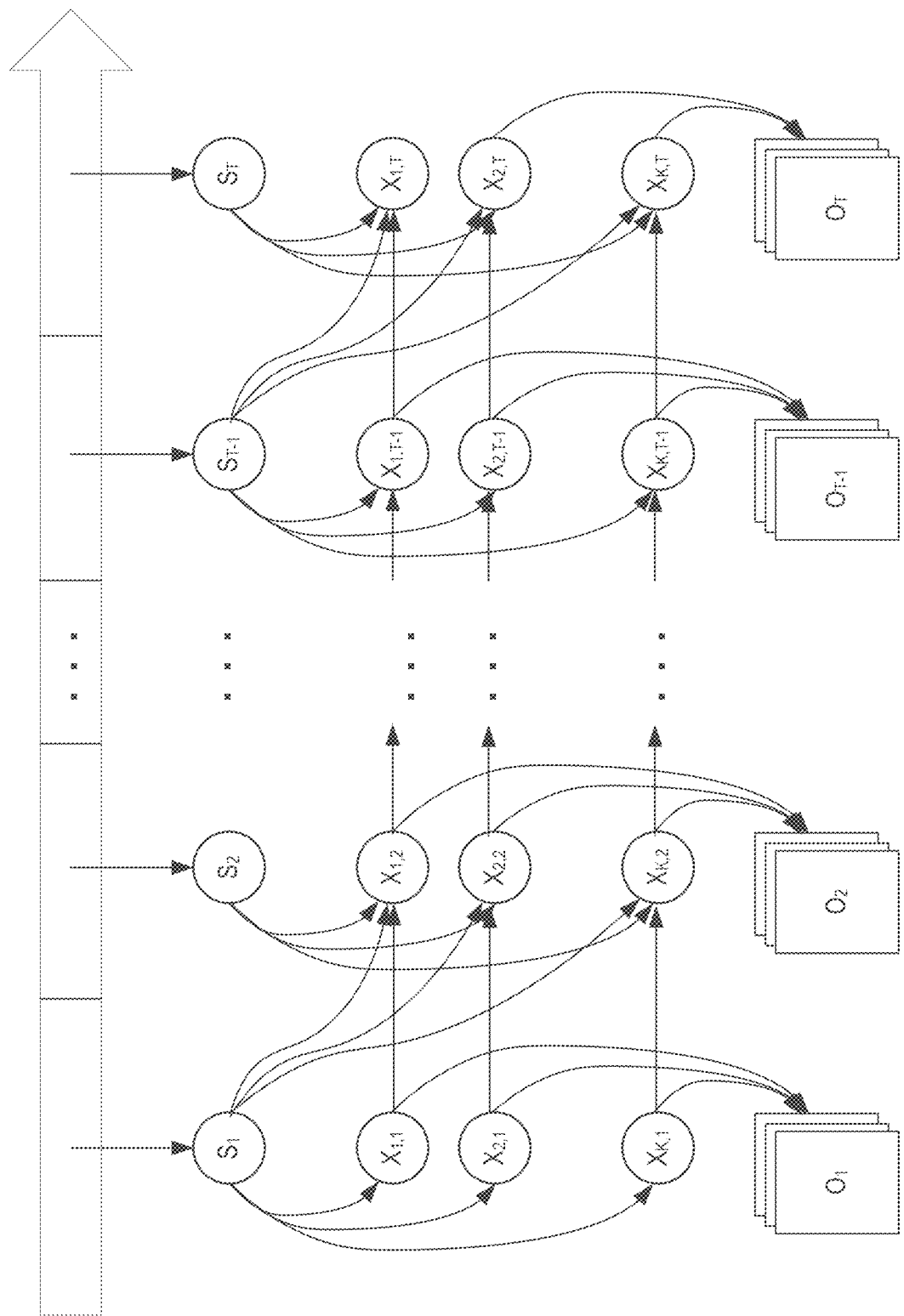
FIG. 9 depicts an example disease progression model.

Behavior scores can serve as an additional input to the Markov Jump Process depicted in FIG. 9, and allow to model the latent health state of an individual on two dimensions: CKD stage (as inferred by the medical history) and an example "healthiness of lifestyle" index, which can be a general measure of how healthy an individual's current lifestyle is. As depicted in the example latent health and behavioral state 1000 depicted in FIG. 10, the trajectory of an individual over time can then be represented in the healthiness/CKD-stage space, which can illuminate a correlation between having a healthier lifestyle and the rate of the progression of CKD slowing—as indicated by the orbit of the trajectory stabilizing around an attractor when the trajectory occupies a space associated with a healthier lifestyle (moving from a healthy lifestyle of Low to High while at the same time seeing a decrease in the CKD stage from II to I). Such information and associations would have not been available without augmenting the disease progression model with the behavioral scores.

The value on the "healthiness of lifestyle" dimension of the latent space can be modeled as a function of behavioral scores. For example, one could model an increase in healthiness of lifestyle as occurring only when both an increase in activity level score and consistency score for weigh-ins is observed, denoting an individual's commitment to improving their lifestyle.

Figure 10:
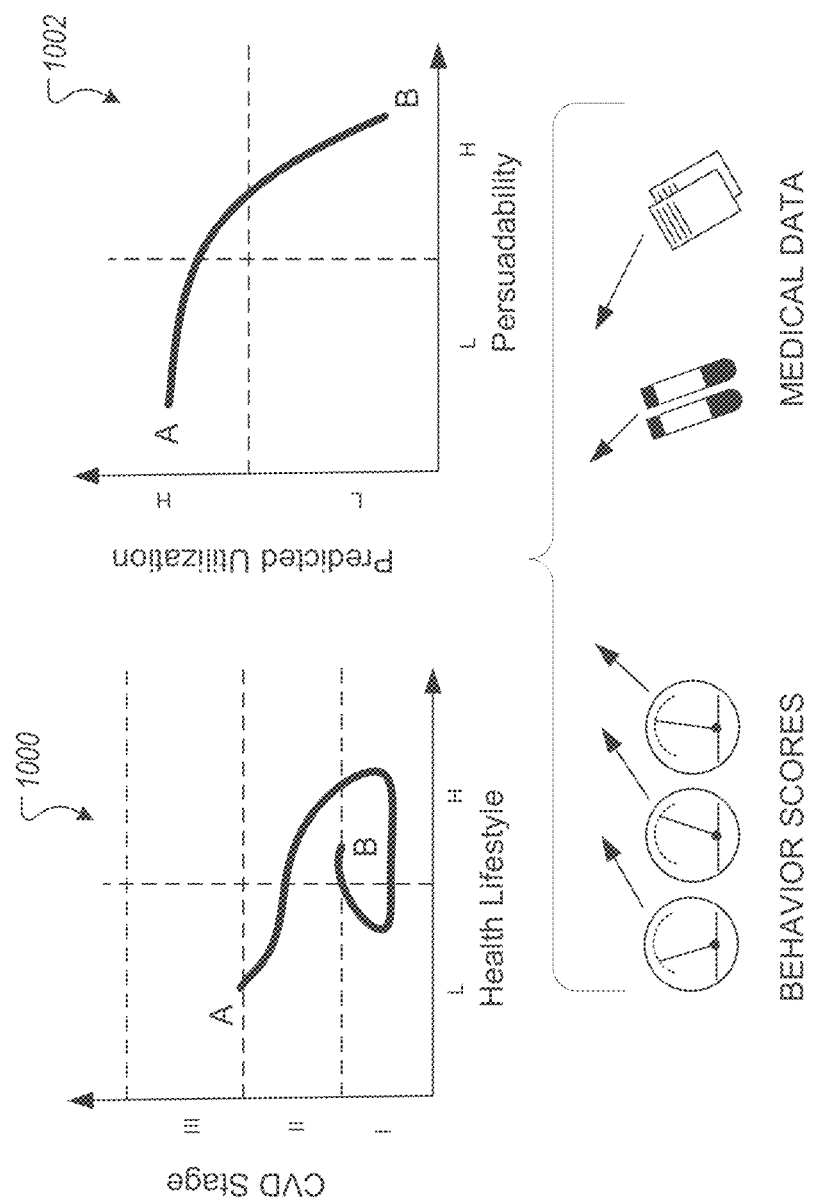
FIG. 10 depicts example latent health and behavioral spaces.

In another example latent health/behavioral space 1002 depicted in FIG. 10, a similar model can be used to infer the state of an individual in the predicted cost/persuadability space. For example, the past medical history of an individual that is input to into a predictive cost model in isolation may model the future patient predicted costs with only a moderate level of accuracy because it does not take into account patient potential to change their behavior, which heavily affect medical costs. When the potential of an individual to be "persuaded" to change their behavior to, for instance, embrace a healthier lifestyle is incorporated into the model, the inference can become much more accurate. Additionally, relationships and correlations between higher persuadability and lower predicted cost can become apparent, as indicated in the example graph 1002. The value on the persuadability behavioral dimension can be modeled based on habit formation scores. Both high receptivity in conjunction with high responsiveness, or medium/high receptivity and habit formation potential can indicate that an individual is more likely to be persuaded to pursue a lifestyle more conducive of better health, hence lower associated medical costs.

Another example of health/behavioral latent space dimensions can include a level of circadian rhythm disruption (as inferred by sleep-related behavioral scores, such as advanced sleep phase, delayed sleep phase, irregular sleep phase, and/or non-24 hour sleep phase) with sleep-related fatigue. Fatigue has high sensitivity for circadian rhythm disruption but low specificity (it could depend on other factors). For this reason, the behavioral dimension related to circadian rhythm computed from sleep can help disambiguate the cause of an observed diagnosis of fatigue between sleep-related and non-sleep-related.

In another example, health/behavior latent space dimensions can include medical dimensions that measures the risk of an individual of getting sick (e.g., the flu) or having other medical ailments/problems/conditions (as inferred from demographics, previous medical history, and/or hospitalization records) and behavioral dimensions that indicate an "immune system response" (as inferred from regular level of activity scores and sleep quality) and persuadability (as inferred from receptivity and responsiveness score). Medical history, demographics and hospitalization can be observed medical data that affect the risk of an individual of getting sick (e.g., contracting the flu). However, the activity level and good sleep quality imply a likely non-debilitated immune system, therefore decreasing the risk. In the same way, a highly persuadable individual is more likely of respond to a vaccination reminder, therefore reducing the risk of contracting an illness (e.g., the flu).

In another example, a health/behavior space can include the progression of Multiple Sclerosis (MS) (or other neurodegenerative disease), computed as function of the medical history, and a "mobility" behavioral dimension, that captures the ability of the individual of deambulate in a self-sufficient way. The mobility dimension can be inferred from the activity level score for stepcounts (how much the individual walks or exercise), and variability of geographic fingerprinting (how often the individual changes location). The mobility behavioral dimension can provide insights in the progression of MS even if the medical history is too coarse-grained to detect any change.

A variety of other latent behavioral and health states can be determined from the behavioral scores and medical data sources. Additional ways to infer the current latent space of an individual from behavioral scores and medical data include, but are not limited to: Tensor PCA, extended Kalman filters, etc.

Referring back to FIG. 1, at step 108 the computer system 100 can use such inferred dynamic hidden states to segment the population into distinct groups based on similarities discovered between their current position in the latent state space 138 and/or their trajectories in the space 140. For example, once individuals from a population are represented in the same reference latent state space, such as latent space 136, their position and trajectory in the space constitute a phenotype that can be used to segment the population using clustering techniques that can place individuals with similar phenotypes in similar groups.

One way to define similarity between individuals is from the state they currently occupy in the latent space. Segments can then be defined through any of a variety of appropriate techniques, such as nearest neighbor (k-means, spectral clustering are other options) clustering after defining a distance metric between phenotypes expressed in the reference latent space. In the case in which phenotypes are distributions over the state space (i.e., individuals are characterized by a distribution of positions or trajectories over the latent health/behavior state space), rather than a single point, the distance metric can be a distributional distance, such as EMO (Earth Mover's Distance). For example, individuals can be segmented into groups based on their current latent states 138 within the example COPD/stress level latent space 136. These groupings may or may not fall along different predefined regions within the space, such as the six different example regions that are depicted—(1) COPD stage I and stress level Low, (2) COPD stage II and stress level Low, (3) COPD stage III and stress level Low, (4) COPD stage I and stress level High, (5) COPD stage II and stress level High, and (6) COPD stage III and stress level High.

An additional and/or alternative option is to define similarity between individuals based on their trajectories over time in the state space (i.e., the computed phenotype captures the evolution of position in the latent space over time), rather than the state currently occupied. In this case the distance metric between trajectories (continuous curves in the state space) can be, for example, the Hausdorff distance, the DTW (dynamic time warping), or a measure of elastic diffeomorphism between the curves. For example, individuals can be segmented into groups based on their trajectories in the space 140, which in this example include linear trajectories (lower left corner), wavy trajectories (upper half), and circular trajectories (lower right corner). These groupings can be based on the trajectories and/or the shape of their trajectory within the latent space 136, and can take into account historical and current trajectory within the space 136. For example, individuals who are exhibiting the same pattern of behavior with regard to their stress level increasing linearly with their COPD stage (lower left corner group) can share commonality that may be beneficial in identifying appropriate interventions that will be helpful to this group, but which may not be helpful to other groups, such as the group with wavy trajectories or the group with circular trajectories.

The computer system 100 can use the segments to target individuals in the same segment with similar interventions, and/or to conduct a more in-depth analysis or a study on them. Other uses of the segments are also possible.

Figure 11:
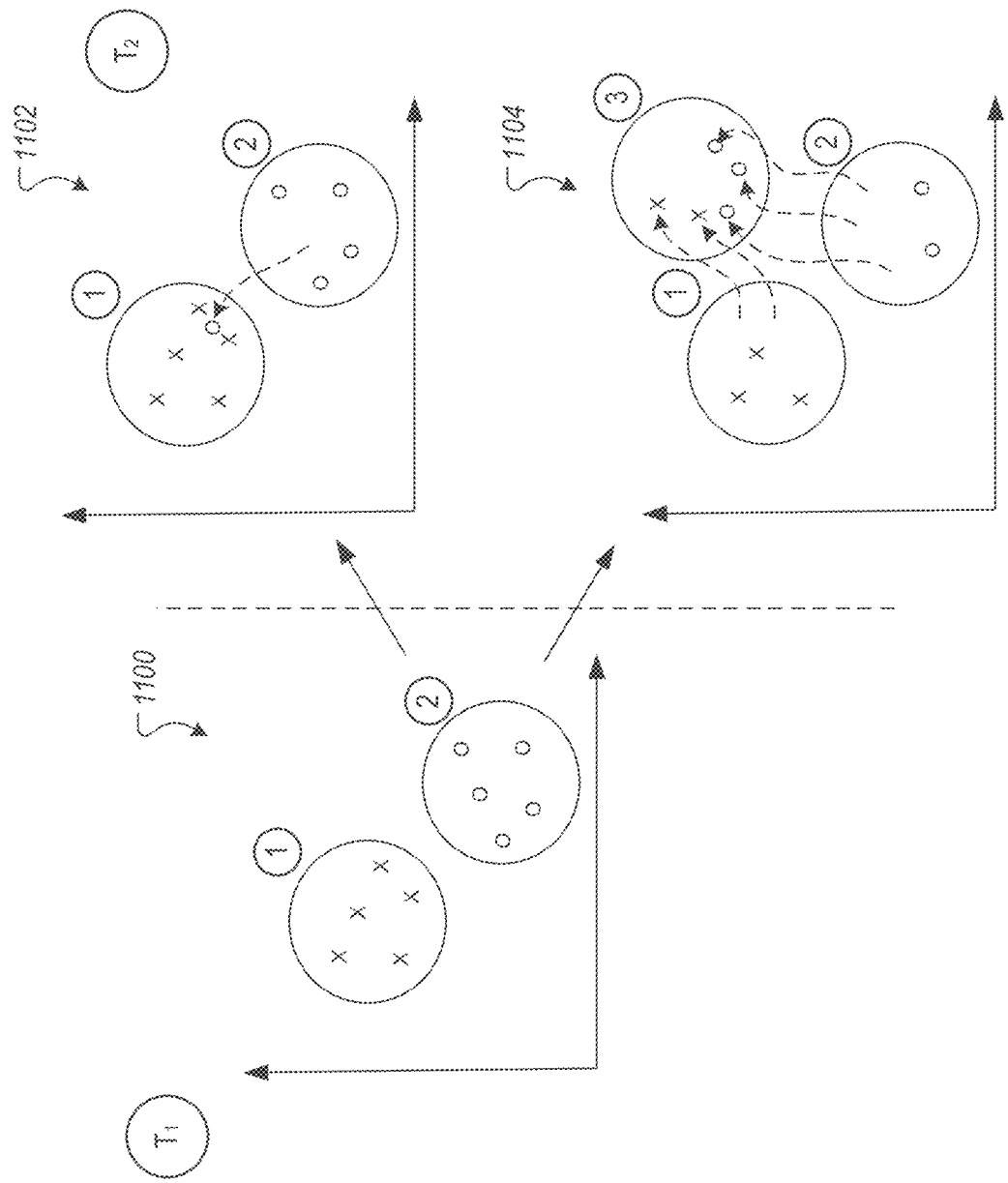
FIG. 11 depicts an example of individual segments changing over time.

Both the location and nature of segments in the state space of the groups and the individuals within them can change dynamically with time, as depicted in FIG. 11, which depicts an example of segments changing over time. Not only can defined segments within the latent space change with time, but individual can dynamically transition between segments. For example, at example time T1 (1100) there are only two well separate clusters of individuals. At time T2, two potential evolutions of the population in the state space are shown: a first evolution (1102) in which clusters are unchanged, but an individual from group 2 has moved to group 1, and a second evolution (1104) in which individuals have collectively moved in the state space creating a new cluster (group 3).

Figure 12:
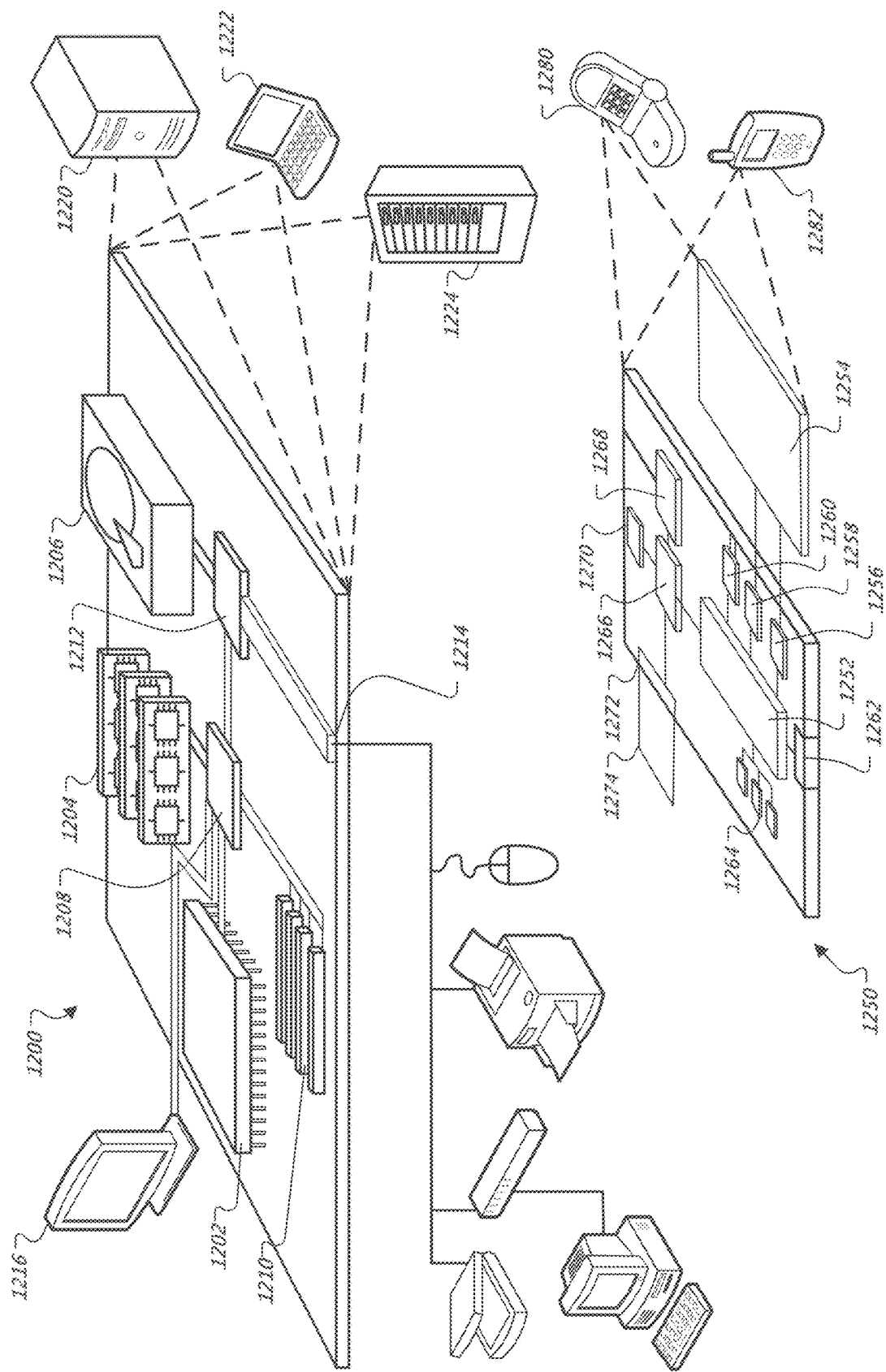
FIG. 12 is a block diagram of example computing devices that may be used to implement the systems and methods described in this document.

FIG. 12 is a block diagram of computing devices 1200, 1250 that may be used to implement the systems and methods described in this document, as either a client or as a server or plurality of servers. Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. Additionally, computing device 1200 or 1250 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, or memory on processor 1202.

The high speed controller 1208 manages bandwidth-intensive operations for the computing device 1200, while the low speed controller 1212 manages lower bandwidth-intensive operations. Such allocation of functions is exemplary only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1250, such as control of individual interfaces, applications run by device 1250, and wireless communication by device 1250.

Processor 1252 may communicate with an individual through control interface 1258 and display interface 1256 coupled to a display 1254. The display 1254 may be, for example, a TFT (Thin-Film-Transistor Liquid Crystal Display) display or an OLEO (Organic Light Emitting Diode) display, or other appropriate display technology. The display interface 1256 may comprise appropriate circuitry for driving the display 1254 to present graphical and other information to an individual. The control interface 1258 may receive commands from an individual and convert them for submission to the processor 1252. In addition, an external interface 1262 may be provided in communication with processor 1252, so as to enable near area communication of device 1250 with other devices. External interface 1262 may provide, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provided as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, or memory on processor 1252 that may be received, for example, over transceiver 1268 or external interface 1262.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TOMA, PDC, WCDMA, CDMA2000, or GPRS, among others. Such communication may occur, for example, through radio-frequency transceiver 1268. In addition, short-range communication may occur, such as using a Bluetooth, Wi-Fi, or other such transceiver (not shown). In addition, GPS (Global Positioning System) receiver module 1270 may provide additional navigation- and location-related wireless data to device 1250, which may be used as appropriate by applications running on device 1250.

Device 1250 may also communicate audibly using audio codec 1260, which may receive spoken information from an individual and convert it to usable digital information. Audio codec 1260 may likewise generate audible sound for an individual, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with an individual, the systems and techniques described here can be implemented on a computer having a display device (e.g., a CRT (cathode ray tube) or LCD (liquid crystal display) monitor) for displaying information to the individual and a keyboard and a pointing device (e.g., a mouse or a trackball) by which the individual can provide input to the computer. Other kinds of devices can be used to provide for interaction with an individual as well; for example, feedback provided to the individual can be any form of sensory feedback (e.g., visual feedback, auditory feedback, or tactile feedback); and input from the individual can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical individual interface or a Web browser through which an individual can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms for performing the systems and methods described in this document may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A method comprising:
    (a) accessing, by a machine learning prediction system, a set of training data for a plurality of users of a population, the set of training data comprising a plurality of time series streams of health events for the plurality of users;
    (b) training, by the machine learning prediction system, a first machine learning model using the accessed set of training data, the first machine learning model configured to predict a health metric;

(c) receiving, by the machine learning prediction system, from a target user, data for the target user, wherein the data comprises a time series stream of health events of the target user;

(d) periodically applying the first trained machine learned model, by the machine learning prediction system, to the received data for the target user to predict a plurality of health metrics for the target user;

(e) combining, by the machine learning prediction system, the plurality of health metrics for the target user with medical data of the target user;

(f) applying, by the machine learning prediction system, a digital filter to the combined plurality of health metrics for the target user and the medical data of the target user to generate a plurality of latent health states for the target user;

(g) using, by the machine learning prediction system, a second machine learning model to predict a latent health space trajectory from the plurality of latent health states of the target user, wherein predicting the latent health space trajectory at least in part comprises modeling a state transition between a first latent health state of the plurality of latent health states and a second latent health state of the plurality of latent health states, wherein the state transition is associated with a difference between the first latent health state of the plurality of latent health states and the second latent health state of the plurality of latent health states;

(h) selecting, by the machine learning prediction system, a health intervention for the target user based at least in part on the latent health space trajectory; and (i) initiating the health intervention on behalf of the target user, wherein the health intervention comprises transmitting a notification to a user device of the target user to cause modification of an interface displayed by the user device to display the notification comprising a warning to the target user of an acute health condition, thereby providing the target user with up-to-date health condition information.

2. The method of claim 1, wherein the health intervention further comprises causing modification of the interface displayed by the user device of the target user to display a notification configured to change a behavior of the target user.

3. The method of claim 1, wherein receiving the data for the target user comprises receiving time series data from one or more of: an activity tracking device, smart clothing with embedded sensors, wireless scale that provides weight measurements, mobile applications running on one or more mobile devices, an electronic dietary log, glucose meters, blood pressure monitors, heart rate monitors, heart rate variability monitors, or other health-related sensors.

4. A non-transitory computer-readable storage medium comprising instructions which, when executed by a processor, cause the processor to perform the operations of:

accessing, by a machine learning prediction system, a set of training-data for a plurality of users of a population, the set of training data comprising a plurality of time series streams of health events for the plurality of users;

training, by the machine learning prediction system, a first machine learning model using the accessed set of training data, the first machine learning model configured to predict a health metric;

receiving, from a target user, data for the target user, wherein the data comprises a time series stream of health events of the target user;

periodically applying the first trained machine learned model to the received data for the target user to predict, by the machine learning prediction system, a plurality of health metrics for the target user;

digitally processing the plurality of health metrics for the target user to generate a plurality of latent health states for the target user;

using a second trained machine learning model to predict a latent health space trajectory from the plurality of latent health states of the target user, wherein predicting the latent health space trajectory at least in part comprises modeling a state transition between a first latent health state of the plurality of latent health states and a second latent health state of the plurality of latent health states, wherein the state transition is associated with a difference between a health metric associated with the first latent health state of the plurality of latent health states and a health metric associated with the second latent health state of the plurality of latent health states;

selecting a health intervention for the target user based at least in part on the latent health space trajectory; and initiating the health intervention on behalf of the target user, wherein the health intervention comprises transmitting a notification to a user device of the target user to cause modification of an interface displayed by the user device to display the notification comprising a warning to the target user of an acute health condition, thereby providing the target user with up-to-date health condition information.

5. The non-transitory computer-readable storage medium of claim 4, wherein the health intervention further comprises causing modification of the interface displayed by the user device of the target user to display a notification configured to change a behavior of the target user.

6. The method of claim 1, wherein the medical data of the target user includes one or more of: lab data for the target user, electronic medical records for the target user, or clinical data for the target user.

7. The method of claim 1, wherein the latent health space trajectory comprises a trajectory of a position of the target user within a latent health-behavior space over a period of time, wherein the latent health-behavior space comprises a plurality of dimensions, wherein a dimension of the plurality of dimensions corresponds to a health-related measurement inferable from a latent health space.

8. The method of claim 7, wherein the period of time comprises a rolling window of time extending from a current time back to a threshold length of time.

9. The method of claim 7, wherein a first dimension of the plurality of dimensions relates to a medical quantity and a second dimension of the plurality of dimensions relates to a behavioral quantity.

10. The method of claim 9, wherein the first dimension includes one or more of: a future medical cost dimension that indicates a projected future medical cost for the target user, a sleep-related fatigue dimension that indicates levels of fatigue resulting from a lack of sleep, a risk of illness dimension that indicates a risk of contracting an illness within a threshold period of time, or a disease progression dimension that indicates a stage of a disease.

11. The method of claim 10, wherein the second dimension includes one or more of: a lifestyle healthiness dimension that indicates a level of lifestyle healthiness for the target user, a circadian rhythm disruption dimension that indicates a level at which a circadian rhythm of the target user is disrupted, an immune system response dimension that indicates how well an immune system of the target user fends off and recovers from illness, a mobility dimension that indicates a level of mobility for the target user, or a persuadability dimension that indicates how well the target user follows health-related direction to improve healthiness.

12. The method of claim 1, wherein the digital filter is a Kalman filter or Tensor Principal Components Analysis (PCA) filter.

13. The method of claim 1, further comprising:
    (i) using a clustering algorithm, placing the target user into a population segment, wherein the clustering algorithm processes the latent health space trajectory of the target user; and
    (k) selecting a health intervention for the population segment.

14. The method of claim 13, wherein the clustering algorithm is k-means clustering or spectral clustering.

15. The method of claim 1, wherein the first machine model is a classifier.

16. The method of claim 15, wherein the health metric is a classification probability or a pair of binary classification outputs.

17. The method of claim 1, wherein the second machine learning model comprises a stochastic method.

18. The method of claim 1, wherein the second machine learning model comprises a particle filter, Markov Jump process, or Hidden Markov Model.

19. A machine learning prediction system, comprising:
    one or more processors; and
    one or more memories storing computer-executable instructions that, when executed, cause the one or more processors to:
    train a first machine learning model on a set of training data for a plurality of users, wherein the set of training data comprises a plurality of time series stream of health events, the first machine learning model configured to generate a health metric;
    periodically process, with the first machine learning model, data for a target user, the data comprising a time series stream of health events from the target user, to generate a set of health metrics for the target user;
    generate a plurality of latent states for the user by (i) combining the set of health metrics with medical data from the target user; and (ii) applying a digital filter to the combined set of health metrics and the medical data from the target user;
    use a second machine learning model to predict a latent health space trajectory from the plurality of latent health states of the target user, wherein predicting the latent health space trajectory at least in part comprises modeling a state transition between first latent health state of the plurality of latent health states and a second latent health state of the plurality of latent health states, wherein the state transition is associated with a difference between the first latent health state of the plurality of latent health states and the second latent health state of the plurality of latent health states;
    select a health intervention for the target user, based at least in part on the latent health space trajectory; and
    initiate the health intervention on behalf of the target user, wherein the health intervention comprises transmitting a notification to a user device of the target user to cause modification of an interface displayed by the user device to display the notification comprising a warning to the target user of an acute health condition, thereby providing the target user with up-to-date health condition information.

20. The machine learning prediction system of claim 19, wherein the computer-executable instructions, when executed, further cause the one or more processors to:
    using a clustering algorithm, place the target user into a population segment, wherein the clustering algorithm processes the latent health space trajectory of the target user.

21. The machine learning prediction system of claim 20, wherein the computer-executable instructions, when executed, further cause the one or more processors to:
    select a health intervention for the population segment.

22. The method of claim 1, wherein the health intervention further comprises one or more of automatically sending a test kit to the target user based on the latent health space trajectory, or automatically scheduling a doctor's appointment with the target user without input from the target user.

23. The non-transitory computer-readable storage medium of claim 4, wherein the health intervention further comprises one or more of automatically sending a test kit to the target user based on the latent health space trajectory, or automatically scheduling a doctor's appointment with the target user without input from the target user.

24. The machine learning prediction system of claim 19, wherein the health intervention further comprises one or more of automatically sending a test kit to the target user based on the latent health space trajectory, or automatically scheduling a doctor's appointment with the target user without input from the target user.

* * * * *